United States Patent
Tu et al.

(10) Patent No.: US 12,037,329 B2
(45) Date of Patent: Jul. 16, 2024

(54) SPHK INHIBITORS AND METHODS OF MAKING AND USING SAME

(71) Applicant: Washington University, St. Louis, MO (US)

(72) Inventors: Zhude Tu, St. Louis, MO (US); Vijai Kumar Reddy Tangadanchu, St. Louis, MO (US); Hao Jiang, St. Louis, MO (US); Buck Rogers, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/820,137

(22) Filed: Aug. 16, 2022

(65) Prior Publication Data

US 2023/0150990 A1    May 18, 2023

Related U.S. Application Data

(60) Provisional application No. 63/229,597, filed on Aug. 5, 2021.

(51) Int. Cl.
*C07D 413/14*    (2006.01)
*C07D 413/10*    (2006.01)

(52) U.S. Cl.
CPC ......... *C07D 413/14* (2013.01); *C07D 413/10* (2013.01)

(58) Field of Classification Search
CPC ............................. C07D 413/10; C07D 413/14
See application file for complete search history.

(56) References Cited

U.S. PATENT DOCUMENTS

2009/0069288 A1* 3/2009 Breinlinger .......... C07D 333/36
                                                                        548/266.8

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Acute Leukemia, Merck Manual (Online Edition) 6 pages, pp. 1-6 (2013).*
Magli et al., Design of Sphingosine Kinases Inhibitors: Challenges and Recent Developments, Current Pharmaceutical Design, 25, pp. 956-968 (2019).*
Lipinski, Christopher A., Drug-like properties and the causes of poor solubility and poor permeability, J. Pharm. Tox. Methods 44 (2000) pp. 235-249.
Irwin, John J. et al., Zinc—A Free Database of Commercially Available Compounds for Virtual Screening, J. Chem. Inf. Model. (2005) 45, pp. 177-182.
Clark, A.J. et al., Prediction of Protein-Ligand Binding Poses via a Combination of Induced Fit Docking and Metadynamics Simulations, J. Chem. Theor. Comput. 12 (2016) 2990-2998.
Deng, Z. et al., Structural Interaction Fingerprint (SIFt): A Novel Method for Analyzing Three-Dimensional Protein-Ligand Binding Interactions, J. Med. Chem. 47 (2004) pp. 337-344.
Sherman, W. et al., Novel Procedure for Modeling Ligand/Receptor Induced Fit Effects, J. Med. Chem. 49 (2006) pp. 534-553.
Teague, Simon J. et al., The Design of Leadlike Combinatorial Libraries, Angew. Chem. Int. Ed. (1999), 38, No. 24, pp. 3743-3748.
Tangadanchu, Vijai Kumar Reddy et al., Structure-activity relationship studies and bioactivity evaluation of 1,2,3-triazole containing analogues as a selective sphingosine kinase-2 inhibitors, European Journal of Medicinal Chemistry, 206 (2020) 112713, pp. 1-17.
Chi, H., Sphingosine-1-phosphate and immune regulation: trafficking and beyond, Trends Pharmacol. Sci. 32 (2011) 16-24.
Takasugi, N. et al., BACE1 activity is modulated by cell-associated sphingosine-1-phosphate, J. Neurosci. 31 (2011) 6850-6857.
Prager, B. et al., Sphingosine 1-phosphate signaling at the blood-brain barrier, Trends Mol. Med. 21 (2015) 354-363.
Heffernan-Stroud, L.A. et al., Sphingosine kinase 1 in cancer, Adv. Cancer Res. 117 (2013) 201-235.
Pyne, N.J. et al., Sphingosine 1-phosphate signalling in cancer, Biochem. Soc. Trans. 40 (2012) 94-100.
Plano, D. et al., Importance of sphingosine kinase (SphK) as a target in developing cancer therapeutics and recent developments in the synthesis of novel SphK inhibitors, J. Med. Chem. 57 (2014) 5509-5524.
Pyne, N.J. et al., Sphingosine 1-phosphate and cancer, Nat. Rev. Cancer 10 (2010) 489-503.
Reid, S.P. et al., Sphingosine kinase 2 is a chikungunya virus host factor co-localized with the viral replication complex, Emerg. Microbes. Infect. 4 (2015) e61.
An, S. et al., Sphingosine 1-phosphate-induced cell proliferation, survival, and related signaling events mediated by G protein-coupled receptors Edg3 and Edg5, J. Biol. Chem. 275 (2000) 288-296.
Olivera, A. et al., Sphingosine Kinase Expression Increases Intracellular Sphingosine-1-Phosphate and Promotes Cell Growth and Survival, J. Cell Biol. 147 (1999) 545-558.
Song, D.D. et al., Regulation and function of sphingosine kinase 2 in diseases, Histol. Histopathol. 33 (2018) 433-445.
Quint, K. et al., The role of sphingosine kinase isoforms and receptors S1P1, S1P2, S1P3, and S1P5 in primary, secondary, and recurrent glioblastomas, Tumour Biol. 35 (2014) 8979-8989.

(Continued)

*Primary Examiner* — Deepak R Rao
(74) *Attorney, Agent, or Firm* — Stinson LLP

(57) ABSTRACT

Among the various aspects of the present disclosure is the provision of SphK inhibitors and methods of making and using same. An aspect of the present disclosure provides for an SphK2 inhibiting agent, wherein the SphK2 inhibiting agent is a 1,2,3-triazole having SphK2 inhibiting activity and SphK2 selectivity.

17 Claims, 8 Drawing Sheets

Specification includes a Sequence Listing.

(56) References Cited

OTHER PUBLICATIONS

Liu, H. et al., Molecular cloning and functional characterization of a novel mammalian sphingosine kinase type 2 isoform, J. Biol. Chem. 275 (2000) 19513-19520.

Neubauer, H.A. et al., Roles, regulation and inhibitors of sphingosine kinase 2, Febs. J. 280 (2013) 5317-5336.

Kunkel, G.T. et al., Targeting the sphingosine-1-phosphate axis in cancer, inflammation and beyond, Nat. Rev. Drug Discov. 12 (2013) 688-702.

Maceyka, M. et al., Sphingosine-1-phosphate signaling and its role in disease, Trends Cell Biol. 22 (2012) 50-60.

Hait, N.C. et al., Regulation of histone acetylation in the nucleus by sphingosine-1-phosphate, Science 325 (2009) 1254-1257.

Igarashi, N. et al., Sphingosine kinase 2 is a nuclear protein and inhibits DNA synthesis, J. Biol. Chem. 278 (2003) 46832-46839.

Ding, G. et al., Protein kinase D-mediated phosphorylation and nuclear export of sphingosine kinase 2, J. Biol. Chem. 282 (2007) 27493-27502.

Okada, T. et al., Involvement of N-terminal-extended form of sphingosine kinase 2 in serum-dependent regulation of cell proliferation and apoptosis, J. Biol. Chem. 280 (2005) 36318-36325.

Rosen, H. et al., Sphingosine 1-phosphate receptor signaling, Annu. Rev. Biochem, 78 (2009) 743-768.

Kharel, Y. et al., Sphingosine Kinase 2 Inhibition and Blood Sphingosine 1-Phosphate Levels, J. Pharmacol. Exp. Ther. 355 (2015) 23-31.

Schnute, M.E. et al., Modulation of cellular S1P levels with a novel, potent and specific inhibitor of sphingosine kinase-1, Biochem. J. 444 (2012) 79-88.

Gustin, D.J. et al., Structure guided design of a series of sphingosine kinase (SphK) inhibitors, Bioorg. Med. Chem. Lett. 23 (2013) 4608-4616.

Patwardhan, N.N. et al., Structure-activity relationship studies and in vivo activity of guanidine-based sphingosine kinase inhibitors: discovery of SphK1- and SphK2-selective inhibitors, J. Med. Chem. 58 (2015) 1879-1899.

Pitman, M.R. et al., A selective ATP-competitive sphingosine kinase inhibitor demonstrates anti-cancer properties, Oncotarget 6 (2015) 7065-7083.

Schnute, M.E. et al., Discovery of a Potent and Selective Sphingosine Kinase 1 Inhibitor through the Molecular Combination of Chemotype-Distinct Screening Hits, J. Med. Chem. 60 (2017) 2562-2572.

French, K.J. et al., Pharmacology and antitumor activity of ABC294640, a selective inhibitor of sphingosine kinase-2, J. Pharmacol. Exp. Ther. 333 (2010) 129-139.

Liu, K. et al., Biological characterization of 3-(2-amino-ethyl)-5-[3-(4-butoxyl-phenyl)-propylidene]-thiazolidine-2,4-dione (K145) as a selective sphingosine kinase-2 inhibitor and anticancer agent, PLOS One 8 (2013) e56471, 13 pages.

Lim K.G. et al., (R)-FTY720 methyl ether is a specific sphingosine kinase 2 inhibitor: Effect on sphingosine kinase 2 expression in HEK 293 cells and actin rearrangement and survival of MCF-7 breast cancer cells, Cell Signal 23 (2011) 1590-1595.

Kim J.W., et al., Synthesis and evaluation of sphingoid analogs as inhibitors of sphingosine kinases, Bioorg. Med. Chem. 13 (2005) 3475-3485.

Raje, M.R. et al., Design, synthesis and biological activity of sphingosine kinase 2 selective inhibitors, Bioorg. Med. Chem. 20 (2012) 183-194.

Childress, E.S. et al., Transforming sphingosine kinase 1 inhibitors into dual and sphingosine kinase 2 selective Inhibitors: Design, Synthesis, and in Vivo Activity, J. Med. Chem. 60 (2017) 3933-3957.

Sibley, C.D. et al., Discovery of a small side cavity in sphingosine kinase 2 that enhances inhibitor potency and selectivity, J. Med. Chem. 63 (2020) 1178-1198.

Rostovtsev, V.V. et al., A stepwise huisgen cycloaddition process: copper(I)-catalyzed regioselective "ligation" of azides and terminal alkynes, Angew Chem. Int. Ed. Engl. 41 (2002) 2596-2599.

Reddy, T. Vijai Kumar et al., Design, synthesis and in vitro biological evaluation of short-chain C12-sphinganine and its 1,2,3-triazole analogs as potential antimicrobial and anti-biofilm agents, Eur. J. Med. Chem. 118 (2016) 98-106.

Schaefer, F.C. et al., Base-catalyzed reaction of nitriles with alcohols. a convenient route to imidates and amidine salts, J. Org. Chem. 26 (1961) 412-418.

Buehrer, B.M. et al., Inhibition of sphingosine kinase in vitro and in platelets. Implications for signal transduction pathways, J. Biol. Chem. 267 (1992) 3154-3159.

Klink, T.A. et al., Evaluating PI3 kinase isoforms using Transcreener ADP assays, J. Biomol. Screen. 13 (2008) 476-485.

Patel, P.R. et al., Identification of potent Yes1 kinase inhibitors using a library screening approach, Bioorg. Med. Chem. Lett. 23 (2013) 4398-4403.

Nagaraj, R. et al., Nuclear localization of mitochondrial TCA cycle enzymes as a critical step in mammalian zygotic genome activation, Cell 168 (2017) 210-223.e211.

Van Brocklyn, J.R. et al., Sphingosine kinase-1 expression correlates with poor survival of patients with glioblastoma multiforme: roles of sphingosine kinase isoforms in growth of glioblastoma cell lines, J. Neuro. Exp. Neuro. 64 (2005) 695-705.

Kornblith, P.L. et al., Chemotherapy for malignant gliomas, J. Neurosurg. 68 (1988) 1-17.

Sordillo, L.A. et al., Sphingosine kinase inhibitors as maintenance therapy of glioblastoma after ceramide-induced response, Anticancer Res. 36 (2016) 2085-2095.

Beljanski, V. et al., A novel sphingosine kinase inhibitor induces autophagy in tumor cells, J. Pharmacol. Exp. Ther. 333 (2010) 454-464.

Antoon, J.W. et al., Targeting NFkB mediated breast cancer chemoresistance through selective inhibition of sphingosine kinase-2, Cancer Biol. Ther. 11 (2011) 678-689.

Sievers, F. et al., Fast, scalable generation of high-quality protein multiple sequence alignments using Clustal Omega, Mol. Syst. Biol. 7 (2011) No. 539, 6 pages.

Schindelin, J. et al., Fiji: an open-source platform for biological-image analysis, Nat. Methods 9 (2012) 676-682.

Elhai, J. et al., Conjugal Transfer of DNA to Cyanobacteria, Methods in Enzymology (1988) 167, pp. 747-754.

Studier, Protein production by auto-induction in high-density shaking cultures (2005) Protein Expr. Purif. 41(1), pp. 207-234.

\* cited by examiner

Fig. 1A

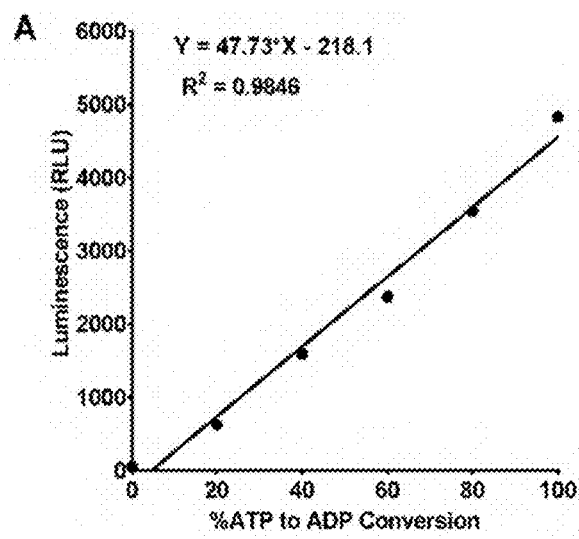
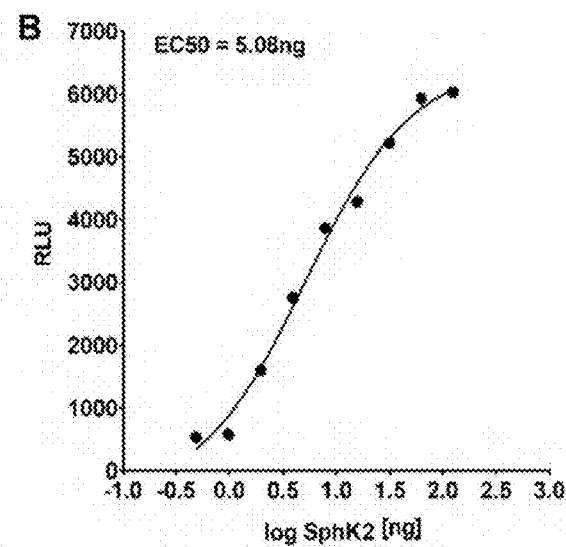
Fig. 4A
Fig. 4B
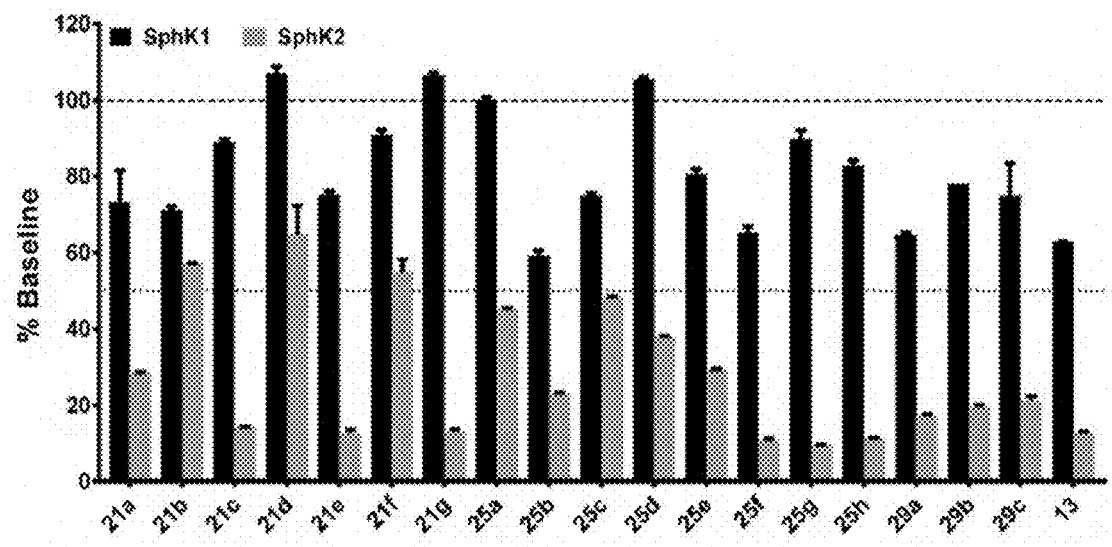
Fig. 5

SPHK INHIBITORS AND METHODS OF MAKING AND USING SAME

CROSS REFERENCE TO RELATED APPLICATIONS

This application claims the benefit of U.S. Provisional Application No. 63/229,597, filed Aug. 5, 2021, the contents of which are incorporated herein in their entirety.

STATEMENT REGARDING FEDERALLY SPONSORED RESEARCH OR DEVELOPMENT

This invention was made with government support under NS103988, NS075527, and EB025815 awarded by the National Institutes of Health. The government has certain rights in the invention.

INCORPORATION OF SEQUENCE LISTING XML

A computer readable form of the Sequence Listing XML containing the file named "3510075.0117 Sequence Listing.xml," which is 3,658 bytes in size (as measured in MICROSOFT WINDOWS® EXPLORER) and was created on Jun. 28, 2022, are provided herein and are herein incorporated by reference. This Sequence Listing consists of SEQ ID NOs: 1-2.

FIELD OF THE INVENTION

The present disclosure generally relates to Sphingosine kinase-2 inhibitors and their therapeutic uses.

BACKGROUND OF THE INVENTION

In the past twenty years, strides have been made targeting sphingolipid signaling as a therapeutic strategy due to its involvement in a wide range of cellular processes. The natural bioactive lipid mediator, sphingosine 1-phosphate (S1P) is a ubiquitous cellular signaling molecule that acts as a critical regulator of many physiological and pathophysiological processes related to, multiple sclerosis, Alzheimer disease, cancer, and viral infections such as Chikungunya virus. In particular, S1P affects proliferation, angiogenesis, and cell survival. The balance between S1P and pro-apoptotic ceramide plays an important role in numerous cancers such as non-small cell lung cancer, gastrointestinal cancer, and glioblastoma.

Sphingosine kinase (SphK) is an important metabolic enzyme that catalyzes the phosphorylation of sphingosine to produce S1P. It plays a pivotal role in the regulation of numerous biological processes through the balance between S1P and ceramides. SphKs exist in two isoforms, SphK1 and SphK2. While SphK1 is 270 amino acids shorter than SphK2, they share approximately 50% sequence identity and the overlapping regions of these two proteins are highly conserved (FIG. 1A). These two isoforms differ in cellular localization and degree of substrate selectivity. In fact, cellular functions of the two isoforms can vary depending on their subcellular localization. SphK1 is a cytosolic enzyme that promotes cell survival and proliferation, whereas some SphK2 resides in the nucleus, but can relocate to the cytosol on phosphorylation. Depending on the subcellular localization, SphK2 can promote either apoptosis or cell proliferation. Due to the critical roles of SphKs in the cell and the importance of the S1P metabolic pathway in various diseases, investigators have focused on the development of dual and specific SphK inhibitors as complementary therapeutic strategies. For example, specific potent SphK1 inhibitors may provide a therapeutic for oncology (D. Plano, et al., J. Med. Chem. 57 (2014) 5509e5524), whereas, recent studies have just begun to explore the role of SphK2 (Y. Kharel, et al., J. Pharmacol. Exp. Therapeut. 355 (2015) 23e31). Therefore, identification of highly potent and selective SphK2 inhibitors would be of great value as pharmacological tools to complement ongoing molecular and genetic studies. Such inhibitors will help unravel the roles of SphK2 in different pathophysiological conditions and explore potential therapeutic applications by targeting SphK2.

There are numerous reports of potent SphK1-selective inhibitors and SphK1/SphK2-dual inhibitors (FIG. 1B). For example, Compounds 1 (PF543, $K_i$ 3.6 nM, >100 fold selective), 2 (Amgen 23), 3 (SLP7111228), and 4 (CB5468139) are the most potent and selective SphK1 inhibitors, and these ligands provided as valuable molecular tools to investigate the S1P pathway (M. E. Schnute, et al., Biochem. J. 444 (2012) 79e88; D. J. Gustin, et al., Bioorg. Med. Chem. Lett 23 (2013) 4608e4616; N. N. Patwardhan, et al., J. Med. Chem. 58 (2015) 1879e1899). Compound 5 (MP-A08) has been reported with $K_i$ values of 27±3 µM and 6.9±0.8 µM against human SphK1 and SphK2, respectively (M. R. Pitman, et al., Oncotarget 6 (2015) 7065e7083). Compound 6 is another potent dual inhibitor (M. E. Schnute, et al., J. Med. Chem. 60 (2017) 2562e2572) with an $IC_{50}$ value of <1.7 nM for both SphK1 and SphK2. Nevertheless, only a limited number of SphK2 inhibitors have been reported with moderate or low selectivity and potency. For example, compound 7 (ABC294640) (K. J. French, et al., J. Pharmacol. Exp. Therapeut. 333 (2010) 129e139), which is currently in phase II clinical trials for the treatment of pancreatic cancer and solid tumors (NCT01488513), exhibits moderate inhibitory activity and selectivity towards SphK2 ($IC_{50}$; SphK2=60 µM; SphK1≤100 µM). Other SphK2 selective inhibitors have been reported, including 8 (K145) (K. Liu, et al., PloS One 8 (2013) e56471), 9 ((R)-FTY720-OMe) (K. G. Lim, et al., Cell. Signal. 23 (2011) 1590e1595), and 10 (SLP120701) (N. N. Patwardhan, et al., J. Med. Chem. 58 (2015) 1879e1899), 11 (SG-12) (J. W. Kim, et al., Bioorg. Med. Chem. 13 (2005) 3475e3485), 12 (trans-12b) (M. R. Raje, et al., Bioorg. Med. Chem. 20 (2012) 183e194), 13 (E. S. Childress, et al., J. Med. Chem. 60 (2017) 3933e3957), and 14 (C. D. Sibley, et al., J. Med. Chem. 63 (2020) 1178e1198). Therefore, adaptable chemical scaffolds for selective SphK2 inhibitors will help identify the structural requirements for designing SphK2 inhibitors and investigating their biological functions.

SUMMARY OF THE INVENTION

Among the various aspects of the present disclosure is the provision of SphK inhibitors and methods of making and using same.

An aspect of the present disclosure provides for an SphK2 inhibiting agent, wherein the SphK2 inhibiting agent is a 1,2,3-triazole having SphK2 inhibiting activity and SphK2 selectivity.

Another aspect of the present disclosure provides for an SphK2 inhibiting agent of formula 21, 25, or 29, or pharmaceutically acceptable salt, solvate, or polymorph thereof or analog or derivative thereof, including all tautomers and stereoisomers, and optionally substituted or optionally functionalized analogs thereof (including all tautomers and stereoisomers).

Yet another aspect of the present disclosure provides for a method of making an SphK inhibiting agent comprising: (1) coupling of amide-oxime derivatives with (S)-2-(1-(tert-butoxycarbonyl)pyrrolidin-2-yl)acetic acid/N-(tert-butoxycarbonyl)-L-proline to make the 1,2,4-oxadiazole motif with polar head groups; (2) employing copper catalyzed version of the Huisgen azide-alkyne cycloaddition protocol to make different 1,2,3-triazole derivatives on the terminal region; and/or (3) deprotecting t-Boc protecting groups with TFA and guanylation of amines followed by deprotection of di t-Boc protecting groups with HCl.

A further aspect of the present disclosure provides for a method of inhibiting SphK2 in a subject comprising administering an SphK2 inhibiting agent as described herein, wherein the subject has an SphK2-associated disease, disorder, or condition.

Yet another aspect of the present disclosure provides for a method of treating an SphK2-associated disease, disorder, or condition comprising administering a therapeutically effective amount of an SphK2 inhibiting agent as described herein to a subject in need thereof, wherein the subject has an SphK2-associated disease, disorder, or condition.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

Figure 1A:
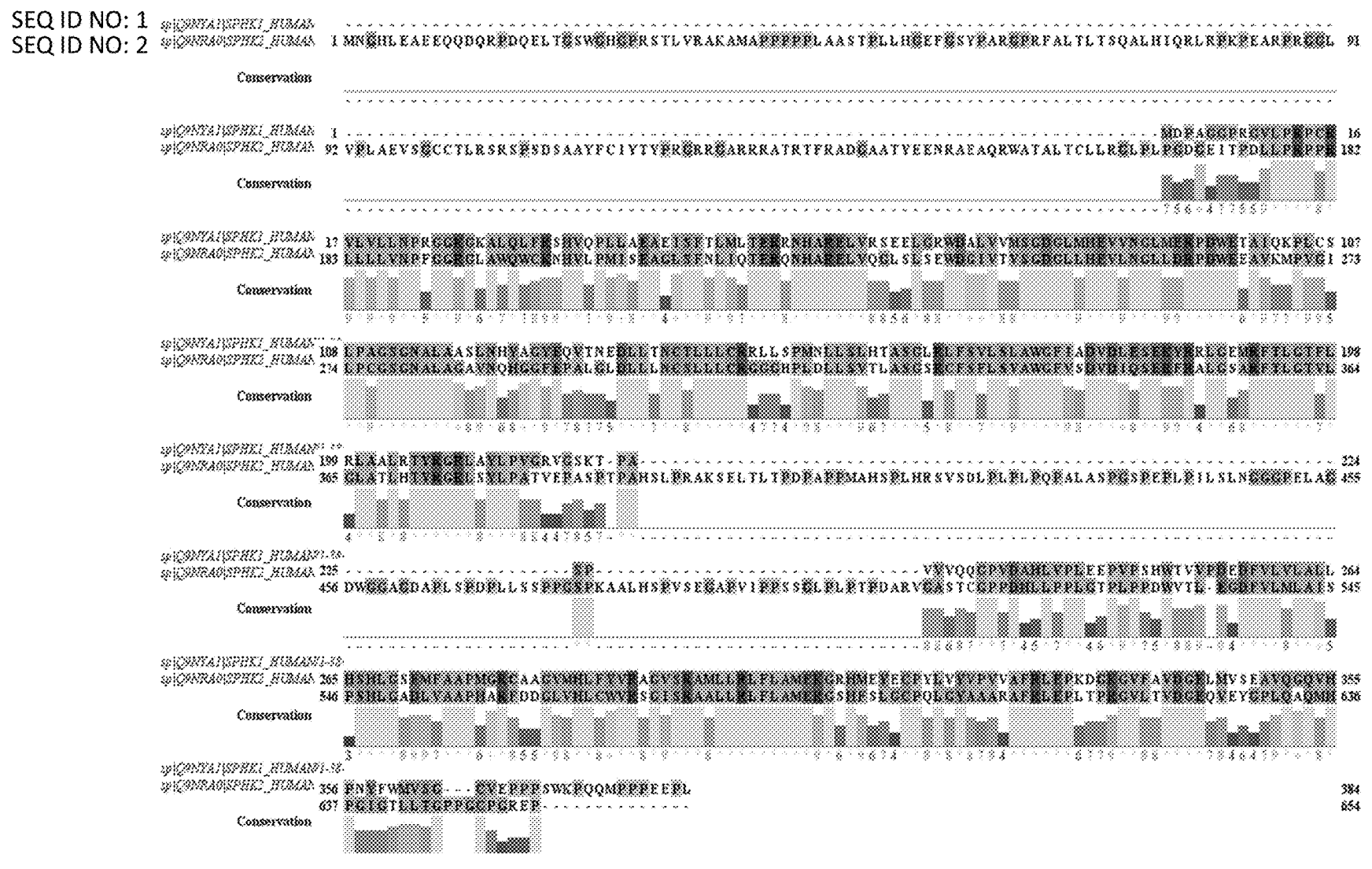

FIG. 1A depicts Protein sequence alignment analysis of human SphK1 (Q9NYA1) and SphK2 (Q9NRAO) using Clustal Omega. SphK1 has 384 amino acids whereas SphK2 has 654 amino acids; however, two proteins are highly conserved in the overlapping regions.

FIG. 4A depicts an ATP-ADP conversion curve. ATP to ADP standard curves were generated in the kinase buffer to evaluate the linearity of the assay and to determine the amount of ADP produced from each tested condition.

FIG. 4B depicts evaluation of ADP-Glo kinase assay performance using recombinant human SphK2. Human recombinant SphK2 showed a dose-response ATP to ADP conversion activity with an $EC_{50}$ of 5.08 ng.

FIG. 5 depicts the inhibition potency and selectivity of all synthesized compounds towards SphK1 and SphK2 activity. The inhibitory activity of all compounds on SphK1 and SphK2 were measured using sphingosine kinase assays and presented as % baseline with no inhibitor added (no treatment control). 125 μM of each compound were tested in triplicate. Error bar indicates S. E. All tested new synthesized compounds showed high potency on SphK2 inhibition (>50% inhibition) and moderate to low potency on SphK1 inhibition (<50% inhibition), indicated that these new compounds are selective for SphK2.

DETAILED DESCRIPTION

Figure 1B:
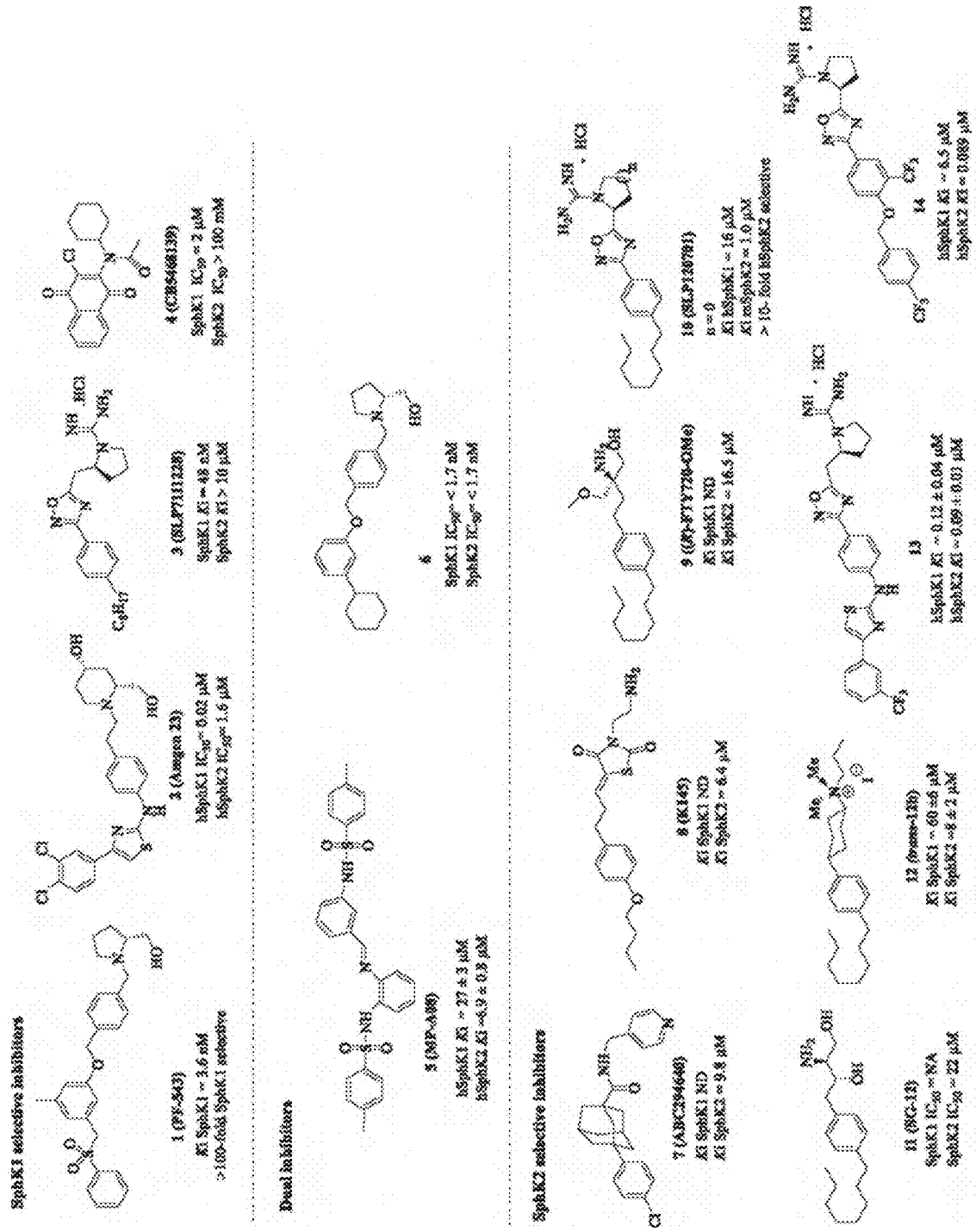
FIG. 1B depicts representative SphK1, dual SphK1/2, SphK2 inhibitors and their inhibitory activities.

The lack of small molecules having highly potent (<100 nM) and selective (>100-fold) SphK2 inhibition prompted the development of improved selective SphK2 inhibitors. Herein is reported efforts to explore a scaffold for SphK2-selective inhibitors including design, synthesis, biological evaluation, molecular docking, and structure-activity relationship analysis of the most potent SphK2-selective inhibitors described to date. All synthesized target compounds were fully characterized by $^1$H NMR, $^{13}$C NMR, and HRMS analysis. The data suggested that several compounds exhibit relatively high potency and high selectivity for SphK2.

The present disclosure is based, at least in part, on the discovery of SphK2 inhibiting agents. As shown herein, SphK2 inhibiting agents displayed moderate to high potency and high specificity to SphK2 over SphK1. All synthesized scaffolds were further evaluated for their in vitro anti-tumor activity using U-251 MG human glioblastoma cells, and the results indicated that three compounds have the highest anti-tumor activity on cell viability, when compared to the standard compound.

The present disclosure provides drugs for treating diseases such as cancer, neurological diseases, heart disease, etc.

Sphingosine Kinase-2 Inhibitors and their Therapeutic Use

Sphingosine kinase (SphK), primarily responsible for the production of Sphingosine-1-phosphate (S1P), plays an important role in many biological and pathobiological processes including cancer, inflammation, neurological and cardiovascular disorders. Due to the critical roles of SphKs in various diseases, investigators have been focusing on the development of dual and specific SphK inhibitors as a complementary therapeutic strategy. Among the two isoforms of SphK, intense investigations have focused on developing SphK1 inhibitors, and only a limited number of SphK2-selective agents have been reported. Further improvements in potency and selectivity of SphK2 are still emerging. Here are identified compounds having potency with high selectivity for SphK2.

Three series of 1,2,3-triazole based SphK2 derivatives were designed and synthesized, and their in vitro SphK2 inhibitory activity was determined employing ADP-Glo kinase assay. The in vitro data suggested that several compounds displayed moderate to high potent and high specificity to SphK2 over SphK1. All synthesized scaffolds were further evaluated for their in vitro anti-tumor activity using U-251 MG human glioblastoma cells, and the results indicated that three compounds have the highest anti-tumor activity on cell viability, when compared to the standard compound.

One aspect of the disclosure is a method of making an SphK inhibiting agent comprising:
(1) coupling of amide-oxime derivatives with (S)-2-(1-(tert-butoxycarbonyl)pyrrolidin-2-yl)acetic acid/N-(tert-butoxycarbonyl)-L-proline to make the 1,2,4-oxadiazole motif with polar head groups;
(2) employing a copper catalyzed version of the Huisgen azide-alkyne cycloaddition protocol to make different 1,2,3-triazole derivatives on the terminal region; and
(3) deprotecting t-Boc protecting groups with TFA and guanylation of amines, followed by deprotection of di t-Boc protecting groups with HCl.

Based on the in vitro SphK2 inhibitory data, the following structure-activity relationship information was observed.
(1) When a methylene linker was introduced between oxadiazole and guanidine polar head group, most of the synthesized target compounds do not show much inhibition towards SphK2, except compound 21g.
(2) In contrast, when a methylene linker between oxadiazole and guanidine polar head group was excluded, most of the compounds exhibited moderate to potent inhibition as well as with higher selectivity against SphK2. The inhibitory potency as follows: non-aromatic>aromatic>heterocyclic substitutions on the terminal region.
(3) Further, when an amidine polar head group was introduced, better improvement in the inhibitory activities was observed with high selectivity towards SphK2. The structure-activity relationship information of these synthesized scaffolds is valuable for guiding the future design of potent and selective SphK2 inhibitors.

All synthesized scaffolds were further evaluated for their in vivo antitumor activity against human malignant glioblastoma tumor U-251 MG cell line. The data suggested that three compounds exhibited high antitumor activity when compared to standard compound. These compounds have high potential to be therapeutic drugs for treating cancer, neurological diseases, heart disease, or other diseases by targeting on SphK2 enzyme and related sphingosine-mediated signaling.

Inhibition using the SphK2 inhibiting agents as described herein can be determined by standard pharmaceutical procedures in assays or cell cultures for determining the $IC_{50}$. The half maximal inhibitory concentration ($IC_{50}$) is a measure of the potency of a substance in inhibiting a specific biological or biochemical function. The $IC_{50}$ is a quantitative measure that indicates how much of a particular inhibitory substance (e.g., pharmaceutical agent or drug) is needed to inhibit, in vitro, a given biological process or biological component by 50%. The biological component could be an enzyme, cell, cell receptor, or microorganism, for example. $IC_{50}$ values are typically expressed as molar concentration. $IC_{50}$ is generally used as a measure of antagonist drug potency in pharmacological research. $IC_{50}$ is comparable to other measures of potency, such as $EC_{50}$ for excitatory drugs. $EC_{50}$ represents the dose or plasma concentration required for obtaining 50% of a maximum effect in vivo. $IC_{50}$ can be determined with functional assays or with competition binding assays.

Sphk2-Associated Disease, Disorder, or Condition

Sphingosine kinase (SphK) is primarily responsible for the production of Sphingosine-1-phosphate (S1P) that plays an important role in many biological and pathobiological processes including cancer, inflammation, neurological and cardiovascular disorders. An SphK2-associated disease, disorder, or condition can be those that have S1P as a regulator. The natural bioactive lipid mediator, sphingosine 1-phosphate (S1P) is a ubiquitous cellular signaling molecule that acts as a critical regulator of many physiological and pathophysiological processes related to, multiple sclerosis, Alzheimer's disease, cancer, and viral infections such as Chikungunya virus. In particular, S1P affects proliferation, angiogenesis, and cell survival. The balance between S1P and pro-apoptotic ceramide plays an important role in numerous cancers such as non-small cell lung cancer, gastrointestinal cancer, breast cancer, prostate cancer, glioblastoma, pancreatic cancer, or solid tumors.

Inhibiting Agents

One aspect of the disclosure is an SphK2 inhibiting agent, wherein the SphK2 inhibiting agent is a 1,2,3-triazole having SphK2 inhibiting activity and SphK2 selectivity. In some embodiments, the SphK2 inhibiting agent is an SphK2 inhibiting agent of formula 21, 25, or 29.

Examples of Sphingosine kinase (SphK) inhibiting agents are described herein.

An SphK2 inhibiting agent can be of formula 21, 25, or 29:

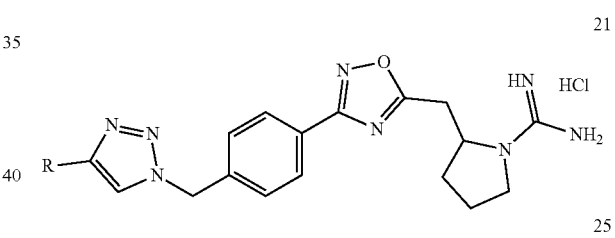

21

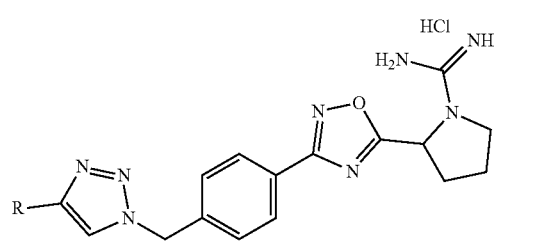

25

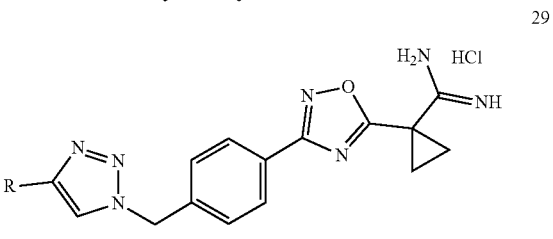

29 or pharmaceutically acceptable salt, solvate, or polymorph thereof or analog or derivative thereof, including all tautomers and stereoisomers, and optionally substituted or optionally functionalized analogs thereof.

For compounds 21, 25, and 29, R can be substituted or unsubstituted aryl, substituted or unsubstituted alkyl, substituted or unsubstituted cycloalkyl, substituted or unsubstituted heterocyclo, or substituted or unsubstituted heteroaryl.
In compounds 21, 25, and 29, R can be phenyl, trifluoromethylphenyl, pyridyl, $C_3$-$C_8$ alkyl, methoxyphenyl, cyclopropyl, thienyl, or fluorophenyl.
R groups can be:
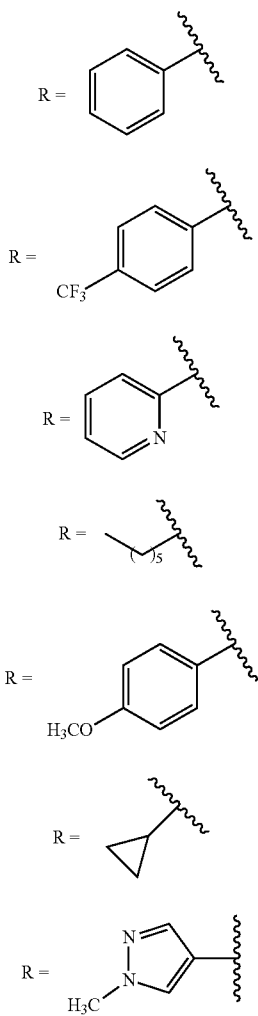
The SphK inhibiting agent can be:
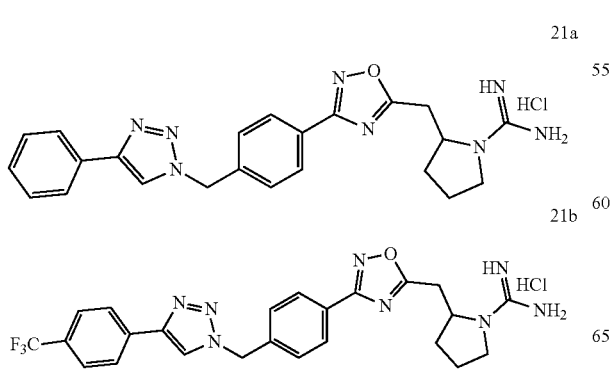
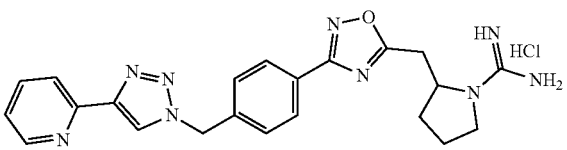
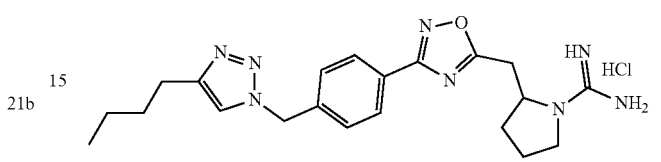
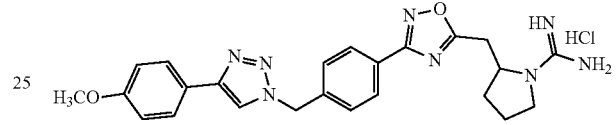
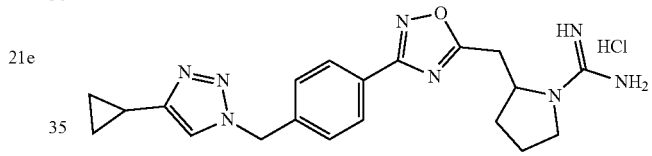
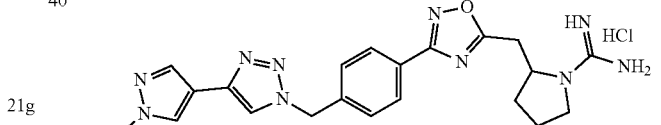
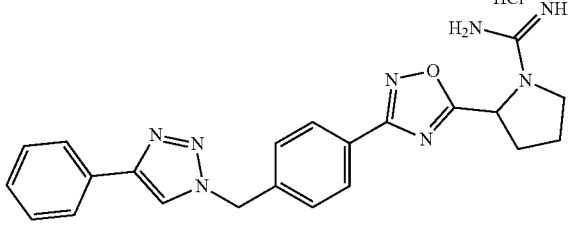
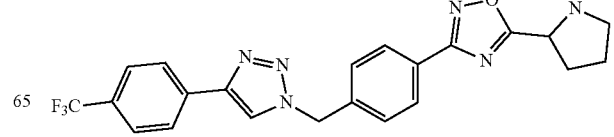

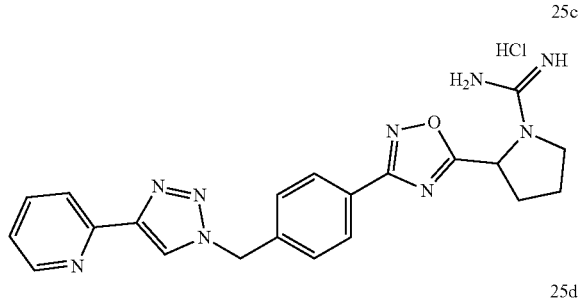

25c

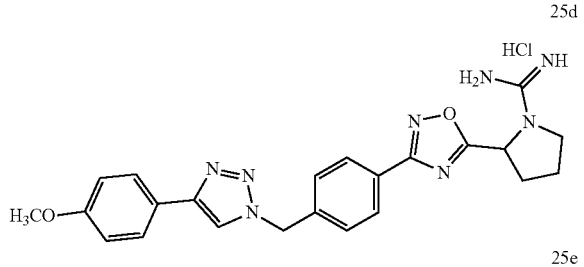

25d

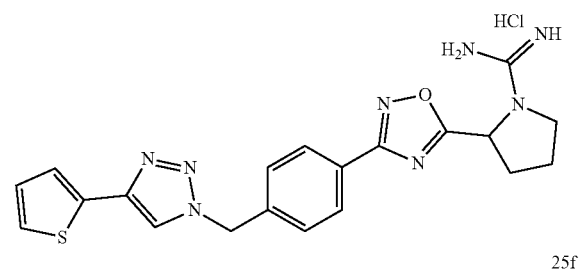

25e

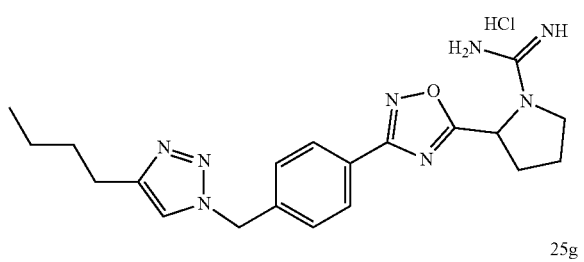

25f

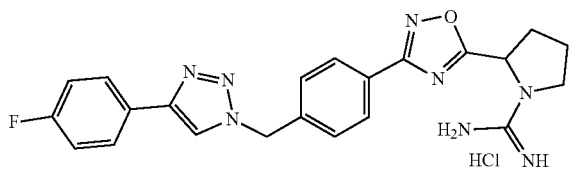

25g

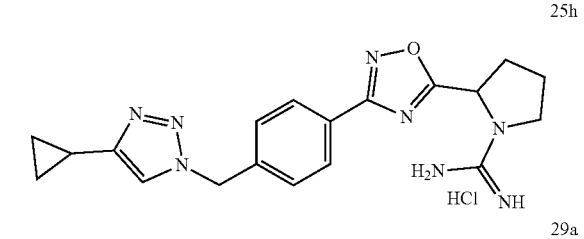

25h

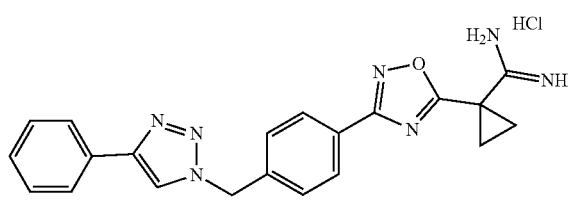

29a

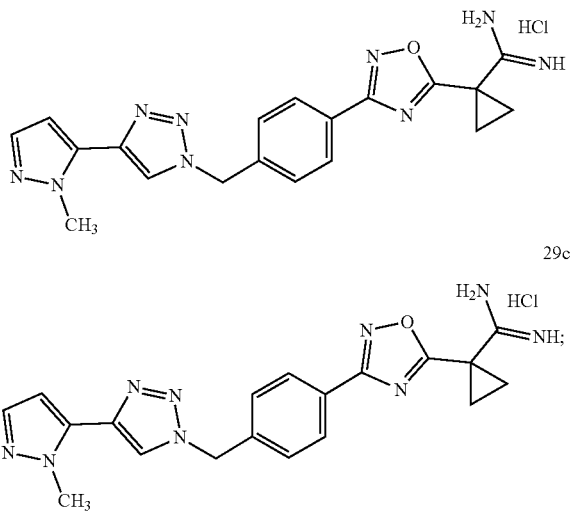

or pharmaceutically acceptable salt, solvate, or polymorph thereof or analog or derivative thereof, including all tautomers and stereoisomers, and optionally substituted or optionally functionalized.

In some embodiments, the SphK2 inhibiting agent has SphK2 inhibiting activity and is selective to SphK2. In some embodiments, the SphK2 inhibiting agent has anti-tumor activity. In some embodiments, the SphK2 inhibiting agent decreases viability of tumor cells.

R groups can be or can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; a $C_{3-10}$cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxyl; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{3-10}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{3-10}$cycloalkyl optionally containing unsaturation or one oxygen or nitrogen atom; heterocyclyl; straight chain or branched $C_{1-10}$alkyl amine; heterocyclic amine; and aryl comprising a phenyl;

and heteroaryl containing from 1 to 4 N, O, or S atoms. Any of the above can be further optionally substituted.

The term "imine" or "imino", as used herein, unless otherwise indicated, can include a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, can include —OH. The "hydroxyl" can be optionally substituted.

The terms "halogen" and "halo", as used herein, unless otherwise indicated, include a chlorine, chloro, Cl; fluorine, fluoro, F; bromine, bromo, Br; or iodine, iodo, or I.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, can include saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_{1-10}$ alkyls include, but are not limited to, -vinyl, -allyl, -1-butenyl, -2-butenyl, -isobutylenyl,-1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated. The "alkyl" can be optionally substituted.

The term "carboxyl", as used herein, unless otherwise indicated, can include a functional group consisting of a carbon atom double bonded to an oxygen atom and single bonded to a hydroxyl group (—COOH). The "carboxyl" can be optionally substituted.

The term "carbonyl", as used herein, unless otherwise indicated, can include a functional group consisting of a carbon atom double-bonded to an oxygen atom (C═O). The "carbonyl" can be optionally substituted.

The term "alkenyl", as used herein, unless otherwise indicated, can include alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, can include alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, can include a functional group derived from an aliphatic carboxylic acid, by removal of the hydroxyl (—OH) group. The "acyl" can be optionally substituted.

The term "alkoxyl", as used herein, unless otherwise indicated, can include O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, -0-2-hexyl, —O-3-hexyl, —O-acetylenyl, —O-propynyl, —O-1-butynyl, —O-2-butynyl, -0-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O— cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxyl can be saturated, partially saturated, or unsaturated. The "alkoxyl" can be optionally substituted.

The term "cycloalkyl", as used herein, unless otherwise indicated, can include an aromatic, a non-aromatic, saturated, partially saturated, or unsaturated, monocyclic or fused, spiro or unfused bicyclic or tricyclic hydrocarbon referred to herein containing a total of from 1 to 10 carbon atoms (e.g., 1 or 2 carbon atoms if there are other heteroatoms in the ring), preferably 3 to 8 ring carbon atoms. Examples of cycloalkyls include, but are not limited to, $C_{3-10}$ cycloalkyl groups include, but are not limited to, -cyclopropyl, -cyclobutyl, -cyclopentyl,-cyclopentadienyl, -cyclohexyl, -cyclohexenyl, -1,3-cyclohexadienyl,-1,4-cyclohexadienyl, -cycloheptyl, -1,3-cycloheptadienyl, -1,3,5-cycloheptatrienyl, -cyclooctyl, and -cyclooctadienyl. The term "cycloalkyl" also can include -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, or —$CH_2$-cyclooctyl. The "cycloalkyl" can be optionally substituted. A "cycloheteroalkyl", as used herein, unless otherwise indicated, can include any of the above with a carbon substituted with a heteroatom (e.g., O, S, N).

The term "heterocyclic" or "heteroaryl", as used herein, unless otherwise indicated, can include an aromatic or non-aromatic cycloalkyl in which one to four of the ring carbon atoms are independently replaced with a heteroatom from the group consisting of O, S, and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, can include a —CN group. The "cyano" can be optionally substituted.

The term "alcohol", as used herein, unless otherwise indicated, can include a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the disclosure in combination with, for example, water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the disclosure. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion, or another counterion. The counterion may be any organic or inorganic moiety that stabilizes the charge on the parent compound. Furthermore, a pharmaceutically acceptable salt may have more than one charged atom in its structure. In instances where multiple charged atoms are part of the pharmaceutically acceptable salt, the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the disclosure. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the disclosure, or a salt thereof, that further can include a stoichiometric or non-stoichiometric amount of water bound by non-covalent intermolecular forces.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing an SphK2-associated disease, disorder, or condition in a subject in need of administration of a therapeutically effective amount of an SphK2 inhibiting agent, so as to inhibit SphK2 or having specificity to SphK2.

One aspect of the disclosure is a method of inhibiting SphK2 in a subject comprising administering an SphK2 inhibiting agent as described herein, wherein the subject has an SphK2-associated disease, disorder, or condition.

Another aspect of the disclosure is a method of treating an SphK2-associated disease, disorder, or condition comprising administering a therapeutically effective amount of an SphK2 inhibiting agent as described herein to a subject in need thereof, wherein the subject has an SphK2-associated disease, disorder, or condition.

Methods described herein are generally performed on a subject in need thereof. A subject in need of the therapeutic methods described herein can be a subject having, diagnosed with, suspected of having, or at risk for developing an SphK2-associated disease, disorder, or condition. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of an SphK2 inhibiting agent is, for example, an amount that would cause the desired therapeutic effect in a subject while minimizing undesired side effects. In various embodiments, an effective amount of an SphK2 inhibiting agent described herein can substantially inhibit an SphK2-associated disease, disorder, or condition, slow the progress of an SphK2-associated disease, disorder, or condition, or limit the development of an SphK2-associated disease, disorder, or condition.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of an SphK2 inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit an SphK2-associated disease, disorder, or condition, slow the progress of an SphK2-associated disease, disorder, or condition, or limit the development of an SphK2-associated disease, disorder, or condition.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of an SphK2 inhibiting agent can occur as a single event or over a time course of treatment. For example, an SphK2 inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for an SphK2 disease, disorder, or condition.

An SphK2 inhibiting agent can be administered simultaneously or sequentially with another agent, such as an antibiotic, an anti-inflammatory, or another agent. For example, an SphK2 inhibiting agent can be administered simultaneously with another agent, such as an antibiotic or an anti-inflammatory. Simultaneous administration can occur through administration of separate compositions, each containing one or more of an SphK2 inhibiting agent, an antibiotic, an anti-inflammatory, or another agent. Simultaneous administration can occur through administration of one composition containing two or more of an SphK2 inhibiting agent, an antibiotic, an anti-inflammatory, or another agent. An SphK2 inhibiting agent can be administered sequentially with an antibiotic, an anti-inflammatory, or another agent. For example, an SphK2 inhibiting agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent;

decrease dosage frequency; improve taste of the product; or improve shelf life of the product.

Screening

Also provided are screening methods to identify compounds having potency with high selectivity for SphK2

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8A to about 15A.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to SphK inhibiting agents, pharmaceutical excipients, delivery components, etc. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing the activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Sphingosine kinase (SphK) is primarily responsible for the production of Sphingosine-1-phosphate (S1P) that plays an important role in many biological and pathobiological processes including cancer, inflammation, neurological and cardiovascular disorders. Most research has focused on developing inhibitors of SphK1 rather than inhibitors of the other isoform SphK2 which has great importance in several pathophysiologic pathways. Exploration of analogues for improving the potency and selectivity of SphK2 inhibitors is critical. Eighteen 1,2,3-triazole analogues for their SphK2 inhibitory activity were designed, synthesized, and evaluated using a ADP-Glo kinase assay, and explored their in vivo anti-tumor bioactivity. Several compounds including 21c, 21e, 21g, 25e-h, and 29a-c have high selectivity for SphK2 over SphK1; compound 21g displayed the highest potency with an $IC_{50}$ value of 0.23 mM. In addition, three compounds 21a, 21b, and 25b have high anti-tumor activity against U-251 MG human glioblastoma cells. Molecular modeling study was performed to elucidate the polar head group and 1,2,3-triazole pharmacophore impact on the SphK2 selectivity.

In summary, a series of potent and selective SphK2 inhibitors were designed and synthesized. All synthesized scaffolds containing guanidine/amidine polar head and 1,2,3-triazole terminal groups. The impact of modifying the polar head group as well as terminal region on the inhibitory activity and selectivity of these compounds towards SphK2 were further investigated. All target compounds were tested for in vitro SphK2 inhibitory activity using a ADP-Glo kinase assay, and antitumor activity using human malignant glioblastoma tumor derived U-251 MG cell line. The in vitro data suggested that compounds 21g, 25d, 25f, 25h, 29a, and 29b were potent towards SphK2 with $IC_{50}$ values of 0.234, 0.266, 0.254, 0.248, 0.261, and 0.269 µM, respectively. Compounds 21c, 21e, 21g, 25e-h, 29a-c displayed high selectivity for SphK2 versus SphK1. Three compounds 21a-b, and 25b also exhibited higher antitumor activity for human malignant glioblastoma tumor U-251 MG cell line when compared with ABC294640. Molecular docking study revealed that polar head group plays an important role in the participation of hydrogen bonding, electrostatic interactions with Asp247, Asp344, and Leu549. In addition, 1,2,3-triazole group fits securely into the hydrophobic "tail" region of the SphK2 binding site, thus might be leads to increased potency toward SphK2 with higher selectivity. Overall, this investigation provides valuable information for further design and development of high potent and selective SphK2 inhibitors which may facilitate the development of therapeutics for treating diseases targeting on SphK2 and related sphingosine-mediated signaling.

The details of these experiments are described in the specific Examples below.

Example 1: Design and Development of Selective SphK2 Inhibitors

Figure 2:
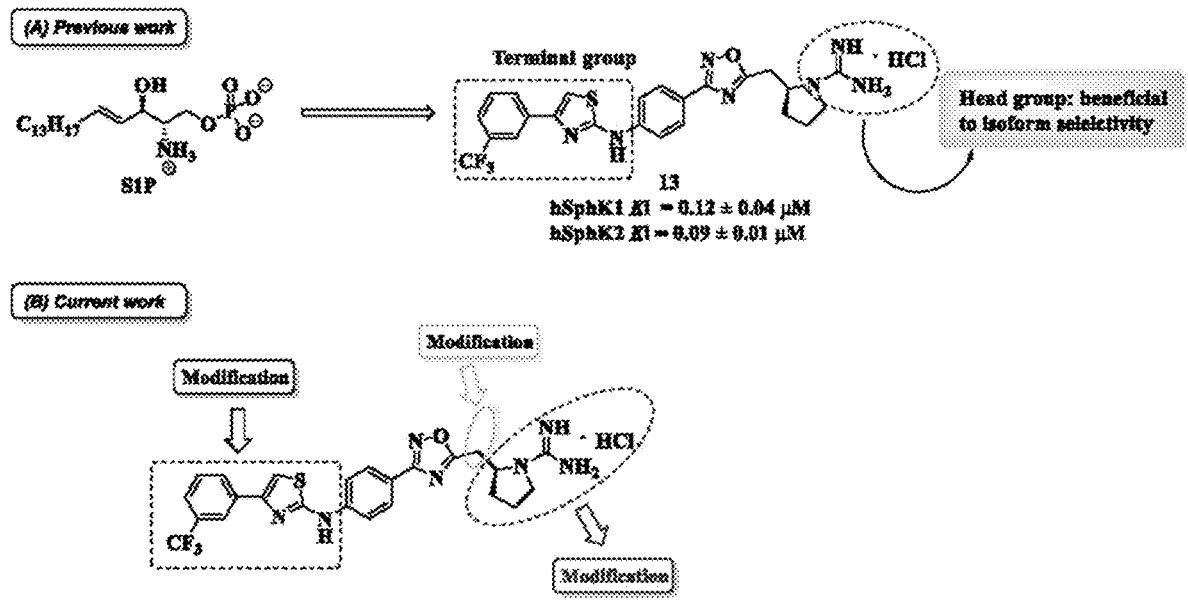
FIG. 2 depicts head and terminal group modifications towards the development of novel SphK2 inhibitors.

A series of SphK2 inhibitors (FIG. 2) were designed based on the structure activity relationship (SAR) analysis of reported data (E. S. Childress, et al., J. Med. Chem. 60 (2017) 3933e3957; C. D. Sibley, et al., J. Med. Chem. 63 (2020) 1178e1198), as well as the reported lead structures of the SphK2 inhibitors shown in FIG. 1B. SphK2-selective inhibitors 13, and 14 with $K_i$ values of 90 nM and 89 nM were recently reported (E. S. Childress, et al., J. Med. Chem. 60 (2017) 3933e3957; C. D. Sibley, et al., J. Med. Chem. 63 (2020) 1178e1198). The inclusion of a methylene unit between the 1,2,4-oxadiazole and head group pyrrolidinyl rings provided a key factor for the inhibitor's selectivity.

Figure 3:
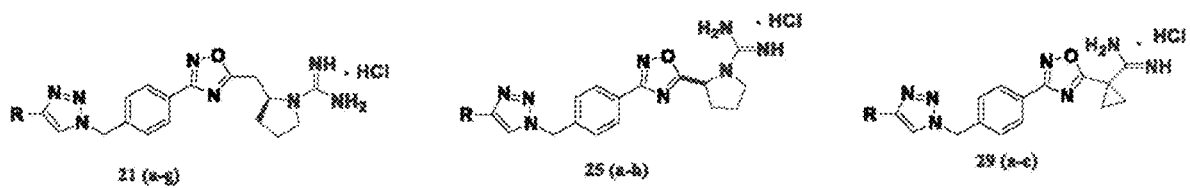
FIG. 3 depicts the design of novel 1,2,3-triazole based SphK2 selective inhibitors.

The effects of different substituents on the phenyl ring in the terminal region by interposing the "aminothiazole terminal" linkage to an oxadiazole phenyl ring were investigated. Positioning of substituents attached to terminal region affected the SphK2 potency and selectivity. Using these strategies, a series of derivatives was designed and prepared by incorporating a 1,2,3-triazole pharmacophore to replace aminothiazole terminal with diverse aryl structures. Further, optimizing the head region of the base structure was focused on. Hence, the inclusion/exclusion of methylene unit and guanidino groups in compounds 13 & 14, prompted us to design derivatives 21a-g, 25a-h, and 29a-c (FIG. 3) bearing guanidino and amidino motifs as the polar head substituents.

Example 2. Synthesis of SphK2 Inhibitors

Guanidine, 1,2,4-oxadiazole and internal phenyl ring moieties reportedly are key features of the sphingosine kinase inhibitor scaffold ((E. S. Childress, et al., J. Med. Chem. 60 (2017) 3933e3957; C. D. Sibley, et al., J. Med. Chem. 63 (2020) 1178e1198),). Therefore, the present study focused on the terminal region by appending 1,2,3-triazole pharmacophore to replace aminothiazole with diverse aryl structures, to study the structure activity relationship. A few modifications were made based on the reported structure of the potent compound 13 to develop SphK2 selective ligands. The synthesis of various substituted 1,2,3-triazole based SphK2 inhibitors are depicted in Scheme 1.

The synthesis of 1,2,3-triazole-containing SphK2 inhibitors commenced from commercially available 4-(hydroxymethyl) benzonitrile 15. The alcohol functionality was then transformed into azide 16 under the condition of 1,8-diazabicyclo [5.4.0]undec-7-ene (DBU) and diphenyl phosphoryl azide (DPPA) in 93% yield. 4-(Azidomethyl)benzonitrile 16 was then treated with hydroxyl-amine hydrochloride and sodium bicarbonate as a base in methanol under reflux conditions to yield amidoxime 17, which was further reacted with homoproline using HCTU and Hunig's base at ~100° C. to afford the 1,2,4-oxadiazole moiety 18 with 56% yield.

The next concern was the divergent synthesis of 1,2,3-triazole based SphK2 inhibitors using 18 as a building block. A copper-catalyzed version of the Huisgen azide-alkyne cycloaddition protocol was employed to synthesize these triazole compounds. Following Huisgen's protocol (V. V. Rostovtsev, et al., Angew. Chem., Int. Ed. Engl. 41 (2002) 2596e2599), the click reaction between compound 18 with different alkynes, namely phenyl acetylene (19a), 1-ethynyl-4-(trifluoromethyl)benzene (19b), 2-ethynylpyridine (19c), hex-1-yne (19d), 1-ethynyl-4-methoxybenzene (19e), ethynylcyclopropane (19f), and 4-ethynyl-1-methyl-1H-pyrazole (19g) in presence of $CuSO_4 \cdot 5H_2O$ and sodium ascorbate as a reducing agent using a mixture of $DCM:H_2O$ (1:1, v/v) furnished the corresponding 1,2,3-triazole analogues with moderate to good isolated yields (45-89%) (T. Vijai Kumar Reddy, et al., Eur. J. Med. Chem. 118 (2016) 98e106). The Boc group in all the above compounds was removed with trifluoroacetic acid and successively reacted with N,N-di-Boc-1H-pyrazole-1-carboxamidine in presence of Hunig's base in acetonitrile at 50° C. to afford di-Boc-protected guanidines 20a-g in low yields. Finally, the desired target compounds had been successfully achieved by removal of di-Boc group using 4 N HCl solution in dioxane. The desired guanidine based 1,2,3-triazoles derivatives 21a-g were generated with good yields (65-91%) and further characterized by $^1H$ NMR, $^{13}C$ NMR, and HRMS analysis.

The synthesis of target compounds 21a-g are shown in Scheme 1 with the following reagents and reaction conditions: (a) DPPA, toluene, rt, 12 h; (b) hydroxylamine hydrochloride, $NaHCO_3$, $CH_3OH$, reflux, 8 h; (c) Boc-L-homoproline, HCTU, DIPEA, DMF, rt to 100° C., 10 h; (d) substituted alkynes; 1:1 $CH_2Cl_2:H_2O$, $CuSO_4 \cdot 5H_2O$, (+)-Sodium-L-ascorbate, rt, 12 h; (e) 1:1 TFA: $CH_2Cl_2$, rt, 6h; (f) N,N-di-Boc-1H-pyrazole-1-carboxamidine, DIPEA, $CH_3CN$, 50° C., 10 h; (g) 4 N HCl, $CH_3OH$, rt, 3h.

Scheme 1

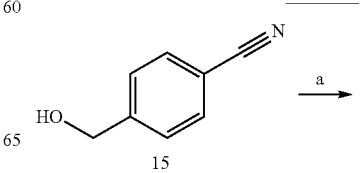

15

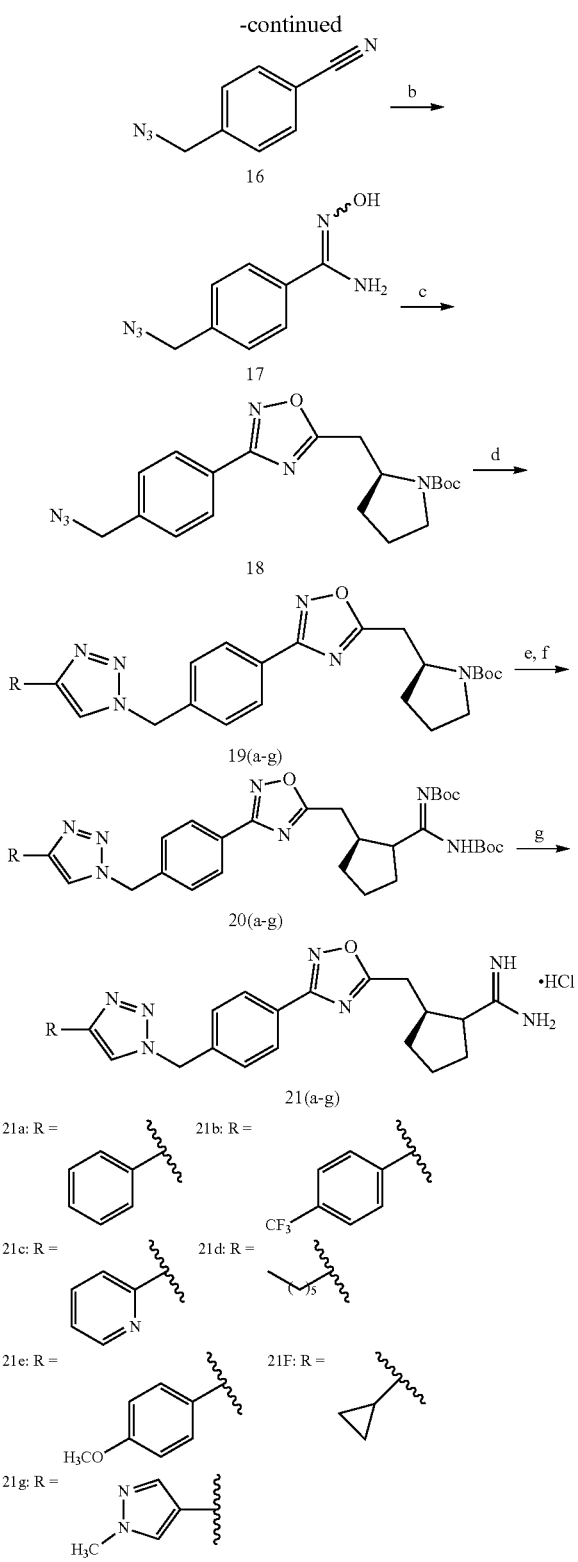

proposed strategy, the synthesis of target compounds 25a-*h* was initiated with intermediate 17, which is reacted with Boc-L-proline in presence of HCTU and Hunig's base at 100° C. to afford the 1,2,4-oxadiazole moiety 22 with high yield (89%).

The next concern was the divergent synthesis of 1,2,3-triazole based SphK2 inhibitors using 22 as a building block. Following Huisgen's protocol, the click reaction between compound 22 with different alkynes, namely phenyl acetylene (23a), 1-ethynyl-4-(trifluoromethyl)benzene (23b), 2-ethynylpyridine (23c), 1-ethynyl-4-methoxybenzene (23d), 2-ethynylthiophene (23e), hex-1-yne (23f), 1-ethynyl-4-fluorobenzene (23g), and ethynylcyclo-propane (23h), in presence of $CuSO_4·5H_2O$ and sodium ascorbate as a reducing agent furnished the corresponding 1,2,3-triazole analogues in good isolated yields (56-85%). The Boc group in all the above compounds was removed with trifluoroacetic acid and successively reacted with N,N-di-Boc-1H-pyrazole-1-carboxamidine in the presence of Hunig's base in acetonitrile at 50° C. to afford bis-Boc-protected guanidines in low yields. Finally, the desired target compounds 25a-*h* were successfully achieved by the removal of the di-Boc group with 4 N HCl solution in dioxane afforded the desired guanidine based 1,2,3-triazoles derivatives in good yields (51-89%).

The synthesis of target compounds 25a-h are shown in Scheme 2 with the following reagents and reaction conditions: (a) Boc-L-proline, HCTU, DIPEA, DMF, rt to 100° C., 10 h; (b) substituted alkynes; 1:1 $CH_2Cl_2:H_2O$, $CuSO_4·5H_2O$, (+)-Sodium-L-ascorbate, rt, 12 h; (c) 1:1 TFA: $CH_2Cl_2$, rt, 6h; (d) N,N'-di-Boc-1H-pyrazole-1-carboxamidine, DIPEA, $CH_3CN$, 50° C., 10 h; (e) 4 N HCl, $CH_3OH$, rt, 3h.

Scheme 2

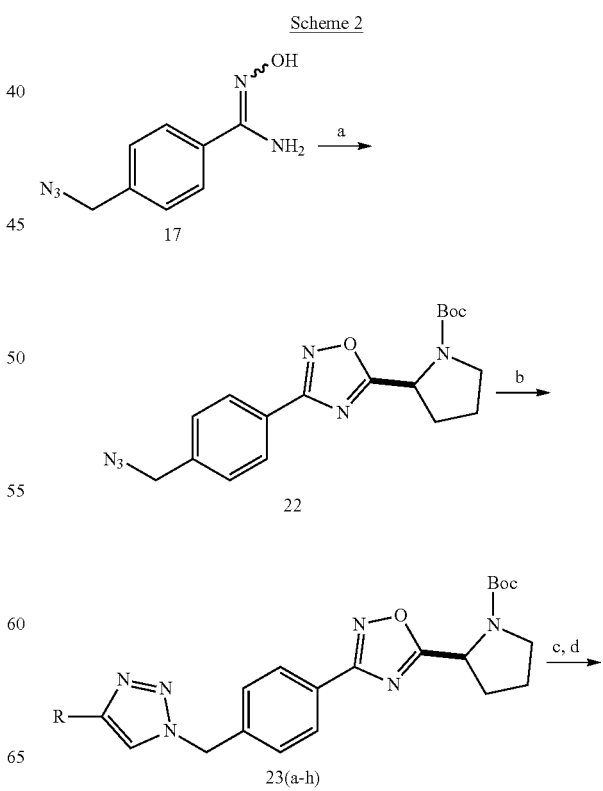

Modifications based on Scheme 1 were made to develop additional ligands for SphK2. The homoproline motif on the right side of the base structure was replaced with proline, while keeping the 1,2,3-triazole pharmacophore on the left side, to study the structure activity relationship. Various substituted 1,2,3-triazole based SphK2 inhibitors were synthesized as outlined in Scheme 2. Moving forward with the

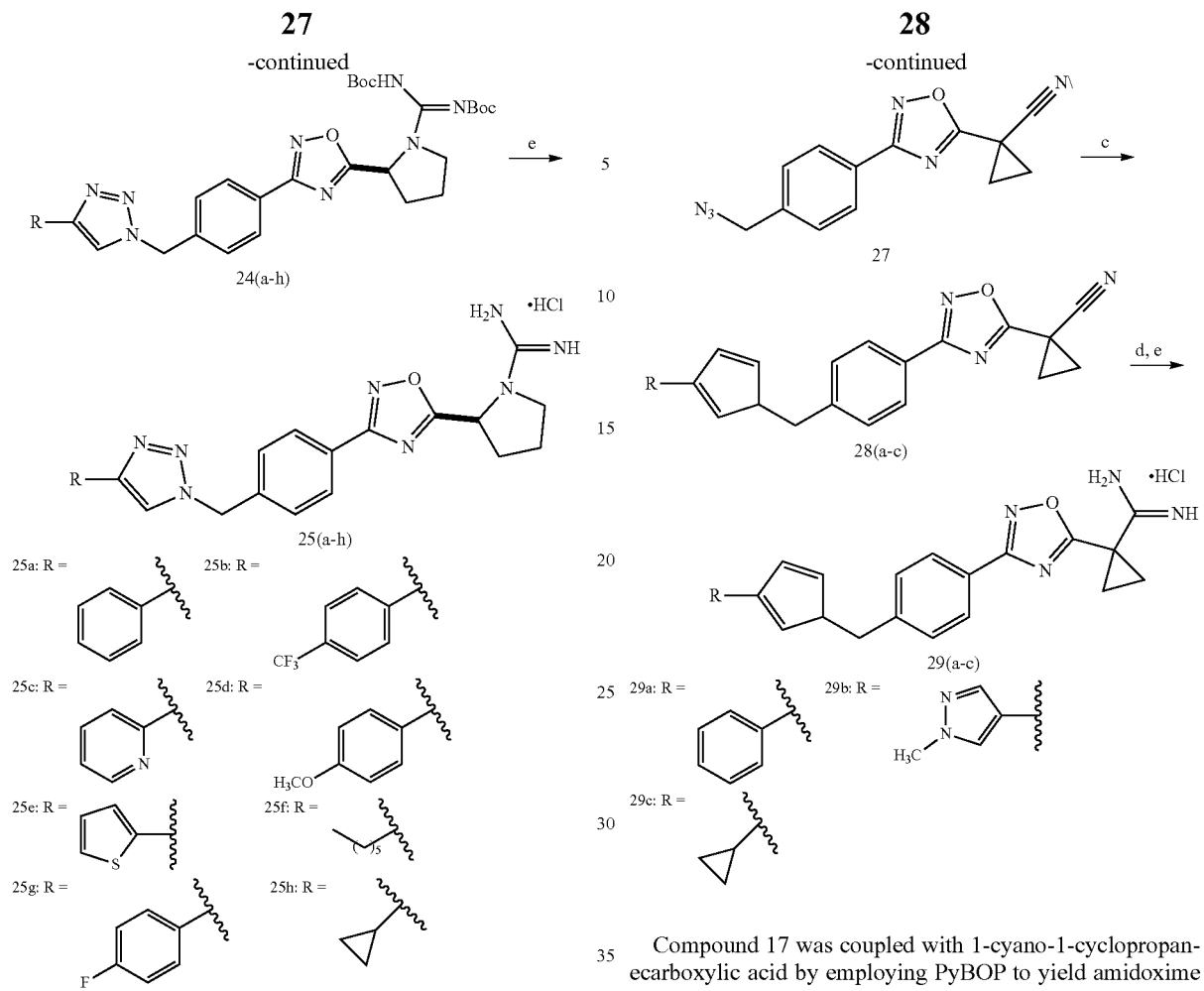

The next approach was to modify the polar head group using amidine motif. Once again, the key intermediate 17 was utilized for the synthesis of amidine based 1,2,3-triazole target compounds 29a-c (Scheme 3).

The synthesis of target compounds 29a-c are shown in Scheme 3 with the following reagents and reaction conditions: (a) 1-cyanocyclopropanecarboxylic acid, PyBop, DIPEA, $CH_2Cl_2$, rt, 4 h; (b) TBAF, THF, rt, 2 h; (c) substituted alkynes; 1:1 $CH_2Cl_2$:$H_2O$, $CuSO_4 \cdot 5H_2O$, (+)-Sodium-L-ascorbate, rt, 12 h; (d) NaOMe, $CH_3OH$, 50° C., 24 h; (e) $NH_4Cl$, 50° C., 1 h.

Scheme 3

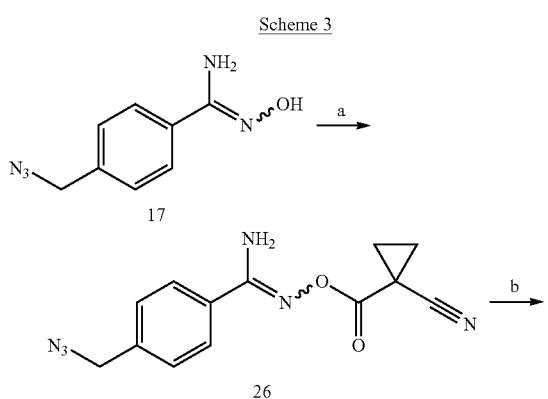

Compound 17 was coupled with 1-cyano-1-cyclopropanecarboxylic acid by employing PyBOP to yield amidoxime compound 26. Cyclization of the coupled amidoxime 26 with tetra-n-butylammonium fluoride (TBAF) gave oxadiazole 27 in 67% yield. The amidine based 1,2,3-triazole SphK2 inhibitors were then synthesized employing 27 as a building block. Again, the click reaction was conducted between 27 with different alkynes in presence of $CuSO_4 \cdot 5H_2O$ and sodium ascorbate as a reducing agent afforded the corresponding 1,2,3-triazole analogues 28a-c in good isolated yields (62-85%). All the above synthesized 1,2,3-triazoles were further subjected to base-catalyzed Pinner conditions (F. C. Schaefer, et al., J. Org. Chem. 26 (1961) 412e418.) to yield the corresponding desired target compounds as amidines 29a-c in moderate yields (51-59%).

Example 3. In Vitro SphK Inhibitory Activity Evaluation and Structure-Activity Relationship Analysis Compounds with high potency and high selectivity for SphK2 were of interest. Therefore, first the inhibition activity of the synthesized compounds was compared with the recent reported potent compound 13 (E. S. Childress, et al., J. Med. Chem. 60 (2017) 3933e3957) against both SphK1 and SphK2 using ADP-Glo Kinase Assay (Promega, Madison, WI). Traditional lipid kinase assays rely on quantifying the amount of phosphate transfer to lipids using lipid extraction and thin-layer chromatography. Although these assays are relative sensitivity and reliable, it is very challenging to separate the product from substrate. They are also expensive and labour-intensive, and difficult to use for high-throughput screening. Another method such as anti-Adenosine Diphosphate (ADP) antibody based assay can be easily used for high-through put screening, but has low dynamic range and limited sensitivity when the concentration of Adenosine Triphosphate (ATP) is too low.

The bioluminescence-based kinase assay such as ADP-Glo assay measures ADP formed from a kinase reaction with a luciferase. Upon the completion of a kinase reaction, the remaining ATP is depleted, the ADP produced in the kinase reaction is then converted to ATP and the detection is based on a sensitive and robust bioluminescence reaction. It has a broad linear range of ATP concentrations and high dynamic range. To determine the inhibition activity of the compounds, the ADP-Glo kinase assay was used which was able to detect down to 20% of 1 µM ATP to ADP conversion (FIG. 4A).

This assay combines the sensitivity and throughput for the detection of ATP conversion, and provides a reliable method to determine the inhibition activity of chemical molecules toward purified kinase, such as SphK1 or SphK2. Today, the ADP-Glo kinase assay is widely used for library screening of kinase inhibitors, ATP/ADP metabolism, and trafficking. It is a convenient method for medium- and high-throughput screening and has an adequate sensitivity to determine the inhibitory activity for different kinase such as SphK1 and SphK2. In the studies, as shown in FIG. 4B, the data indicated that the recombinant human SphK2 has dose-response activity of ATP conversion with an $EC_{50}$ of 5.08 ng. After incubation with the optimized concentration (125 µM) of each synthesized compound, all compounds showed significant reduction of SphK2 activity as expected, with most of them showed more than a 50% reduction. Meanwhile, all synthesized compounds only showed moderate to no effect on SphK1 activity (FIG. 5). The results indicated that all compounds are more favourable to inhibit SphK2 than SphK1 activity, and thus more selective to SphK2. Among all compounds, 21c, 21e, 21g, 25e-$h$, 29a-$c$ displayed the highest specificity for SphK2 inhibition. In contrast, 21b, 21d, 21f, and 25c exhibited the lowest specificity to SphK2.

The $IC_{50}$ values of compounds toward SphK2 using ADP-Glo assay are tabulated in Tables 1-3. The results for derivatives 21a-g bearing a 1,2,3-triazole at the terminal region as well as a methylene linker between oxadiazole and a guanidine on the polar head are shown in Table 1. Compound 13 served as a reference standard compound for the inhibitory activity determination in the biological evaluation in vitro (E. S. Childress, et al., J. Med. Chem. 60 (2017) 3933e3957).

TABLE 1

SphK2 inhibitory activity of synthesized target compounds 21a-g

| Compounds | R | SphK2 $IC_{50}$ (µM) | cLogP[a] |
|---|---|---|---|
| 21a | phenyl | 0.396 | 1.97 |
| 21b | 4-CF$_3$-phenyl | — | 2.92 |
| 21c | 2-pyridyl | 0.452 | 0.86 |
| 21d | butyl | — | 1.73 |
| 21e | 4-methoxyphenyl | 0.640 | 1.96 |
| 21f | cyclopropyl | — | 0.59 |
| 21g | 1-methylpyrazol-4-yl | 0.234 | 0.17 |
| Compound 13 (std) | | 0.280 | 5.18 |

[a] cLogP was calculated from Chemdraw Professional 19.0; compound 13 served as a reference standard compound.

The in vitro SphK2 inhibition data showed that compounds 21b, 21d, 21f with para-trifluoromethyl phenyl, butyl, and cyclopropyl substituted groups respectively on the 1,2,3-triazole terminal region, resulted in no inhibitory activity, also no selectivity towards SphK2 (FIG. 5). In contrast, the compounds bearing a phenyl (21a), 2-pyridyl (21c), and para-methoxy phenyl (21e) substituted groups on the 1,2,3-triazole ring exhibited good to moderate inhibitory activities towards SphK2 with $IC_{50}$ values of 0.396 µM, 0.452 µM, 0.640 µM, respectively, when compared with the standard reference compound 13 ($IC_{50}$=0.28 µM). It is noteworthy that the compound having a 1-methylpyrazole substituted group on the 1,2,3-triazole terminal (21g), exhibited potent SphK2 inhibitory activity with an $IC_{50}$ value of 0.234 µM which was more potent than the reference compound 13 ($IC_{50}$ 0.28 µM), and had high selectivity for SphK2 over SphK1 (FIG. 5).

The further exploration of analogues focused on the polar head group without a methylene linker between oxadiazole and guanidine motif, and the results are shown in Table 2. From one side, as shown in Scheme 2, first a guanidine group was retained on the polar head region, and studied the impact of various substituted groups on the 1,2,3-triazole terminal region 25a-*h*. All synthesized analogues 25a-*h* in this series had moderate to high potent SphK2 inhibitory activity, except compound 25a. Particularly, compounds having heterocyclic substituents (25c&e) on the 1,2,3-triazole ring demonstrated moderate inhibition towards SphK2 with $IC_{50}$ values of 0.900 µM, 0.687 µM, respectively. A further improvement in SphK2 inhibitory activity was observed with compounds bearing either an electron-donating (25d: $IC_{50}$=0.266 µM) or an electron-withdrawing substituted group (25b: $IC_{50}$=0.359 µM; 25g: $IC_{50}$=0.391 µM) on the aromatic ring of the 1,2,3-trizole terminal region. Interestingly, compounds containing non-aromatic substituents on the 1,2,3-trizole motif, such as compounds 25f&*h* proved to be the most potent SphK2 inhibitors in this series with $IC_{50}$ values of 0.254 µM and 0.248 µM, respectively. In addition, compounds 25f&*h* also displayed high selective for SphK2 over SphK1 (FIG. 5).

TABLE 2

SphK2 inhibitory activity of guanidine-based target compounds 25a-h

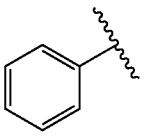 [SMILES: *c1ccccc1]

25(a-h)

| Compounds | R | SphK2 $IC_{50}$ (µM) | cLogP[a] |
|---|---|---|---|
| 25a | 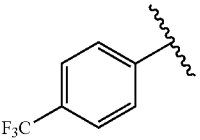 | — | 1.87 |
| 25b | 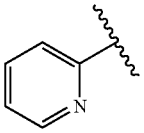 [SMILES: *c1ccccn1] | 0.359 | 2.82 |
| 25c | 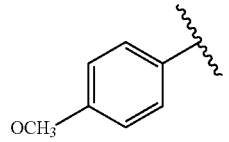 | 0.909 | 0.76 |
| 25d | 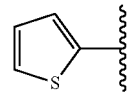 | 0.266 | 1.86 |
| 25e | 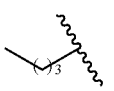 | 0.687 | 1.77 |
| 25f | 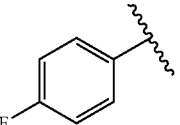 | 0.254 | 1.63 |
| 25g | 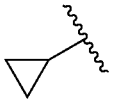 | 0.391 | 2.05 |
| 25h | 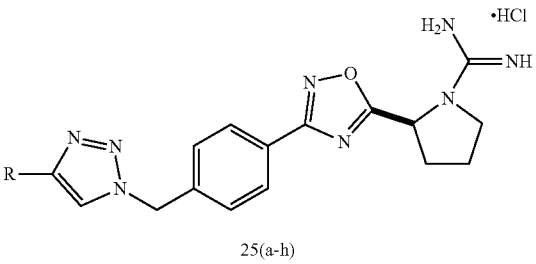 | 0.248 | 0.49 |
| Compound 13 (std) | | 0.280 | 5.18 |

[a]cLogP was calculated from Chemdraw Professional 19.0; compound 13 served as a reference standard compound.

The impact of polar head group with an amidine motif was next investigated; compounds 29a-*c* were synthesized and evaluated for their in vitro SphK2 inhibitory activity, and the results are tabulated in Table 3. The introduction of an amidine polar head group containing 1,2,3-triazoles generally favoured SphK2 inhibition with higher selectivity over SphK1. For example, the inhibitory activities of compounds 29a, and 29b were improved with an $IC_{50}$ values of 0.261 µM, 0.269 µM respectively. However, compound 29c bearing a cyclopropyl substitution on 1,2,3-triazole terminal displayed moderate inhibition ($IC_{50}$=0.717 µM), in comparison to reference standard compound 13.

TABLE 3

SphK2 inhibitory activity of amidine based target compounds 29a-c

[Structure of 29(a-c): triazole-R linked via CH2 to phenyl-oxadiazole-C(cyclopropyl)(C(=NH)NH2·HCl)]

| Compounds | R | SphK2 IC$_{50}$ (μM) | cLogP[a] |
|---|---|---|---|
| 29a | phenyl | 0.261 | 1.49 |
| 29b | 1-methyl-1H-pyrazol-4-yl | 0.269 | −0.31 |
| 29c | cyclopropyl | 0.717 | 0.10 |
| Compound 13 (std) | | 0.280 | 5.18 |

[a]cLogP was calculated from Chemdraw Professional 19.0; compound 13 served as a reference standard compound.

Finally, from the in vitro SphK2 inhibitory data shown in Tables 1-3, the following structure-activity relationship information was observed: (a) an introduced methylene linker between oxadiazole and guanidine polar head group, most of the synthesized target compounds did not increase inhibition towards SphK2, except compound 21g; (b) excluding a methylene linker between oxadiazole and guanidine polar head group led to potent inhibition and higher selectivity of most compounds against SphK2. The inhibitory potency is as follows: non-aromatic>aromatic>heterocyclic substitutions on the terminal region; (c) further, introducing an amidine polar head group increased the inhibitory activity of compounds 29a and 29b with an IC$_{50}$ values of 0.261 μM, 0.269 μM respectively with highly selective towards SphK2. The structure-activity relationship information of this synthesized scaffold provides a valuable guide for the future design of potent and selective SphK2 inhibitors.

Example 4. Modeling Docking Study

In addition to the SAR information derived from the medicinal chemistry efforts outlined above, potential binding modes for compound 29a within SphK2 were evaluated utilizing a combination of homology modeling and flexible receptor docking. The approach was inspired by recent efforts that have enabled significant improvements in SphK2 inhibitor potency and selectivity (C. D. Sibley, et al., J. Med. Chem. 63 (2020) 1178e1198). Given the challenges of accurate homology modeling and ligand binding mode prediction, the utility of modern tools was investigated for identifying possible binding modes for compound 29a. Recently, significant advances have enabled more accurate prediction of protein structure determination via template-based methods through the use iterative Monte Carlo simulations and model refinement with molecular dynamics.

Figure 6:
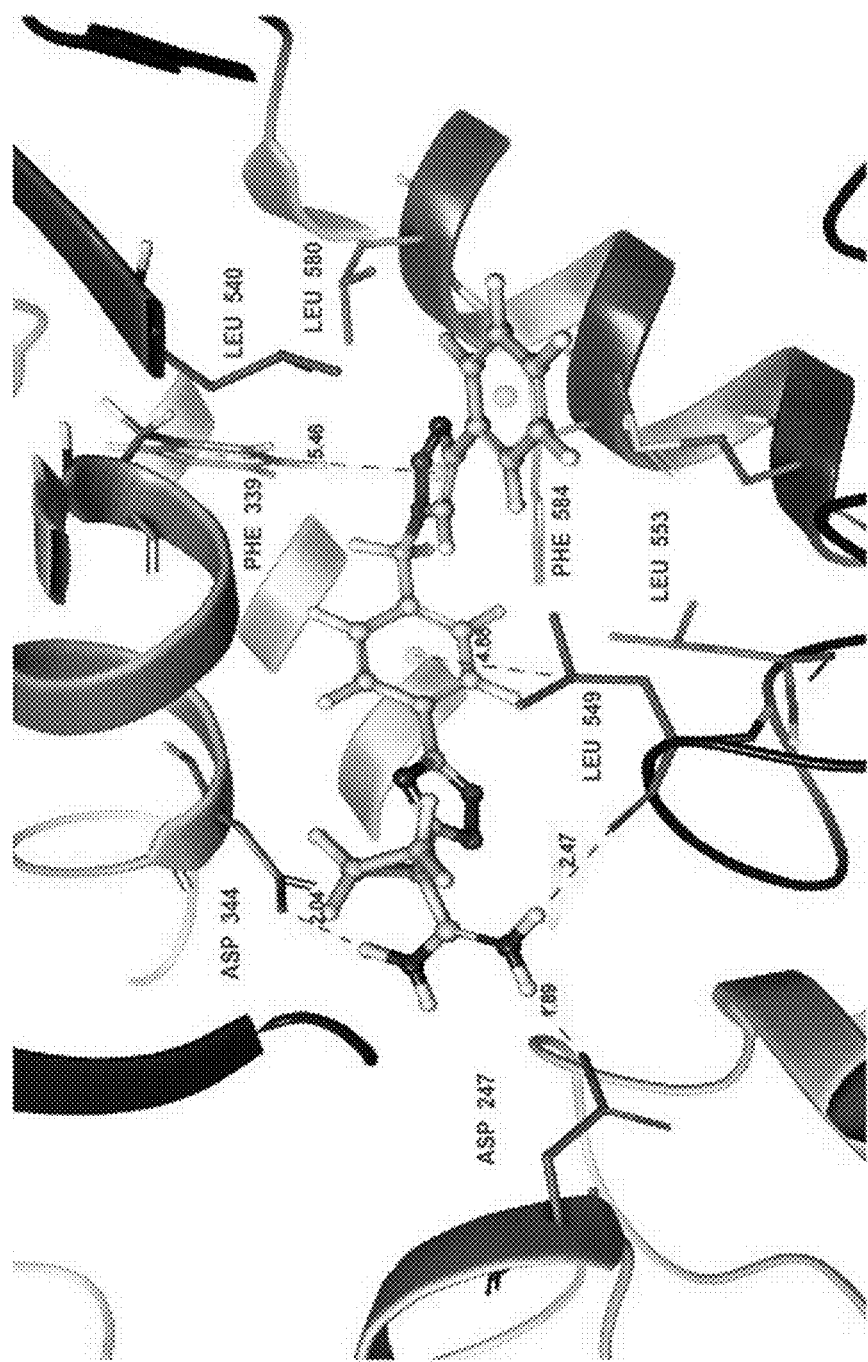
FIG. 6 depicts top-scoring binding pose of compound 29a within the homology model of SphK2. Key interactions and their respective distances are highlighted with dashed lines (distance is represented in angstroms).

Through the use of I-TASSAR, a full-length homology model of SphK2 was constructed and then subjected to induced fit docking and metadynamics to identify likely binding poses for compound 29a (A. J. Clark, et al., J. Chem. Theor. Comput. 12 (2016) 2990e2998). An approach was employed that yielded a total of six high-scoring (IFD score) non-degenerate poses as identified by structural interaction fingerprints and following metadynamics, the top-scoring pose shown in FIG. 6 (Pose Score) was selected for further analysis. The identified binding pose is comprised of key hydrogen bonding and electrostatic interactions between the polar amidine head piece of compound 29a and Asp247, Asp344. Additionally, the amidine moiety of compound 29a participates in a hydrogen bond with the amide backbone of Leu549 which may be further enabled by the methylene-cyclopropyl ground found on compound 29a. Contacts within the hydrophobic core and tail region are in line with previous observations and are comprised of hydrophobic and pi-pi interactions with Leu549, Leu540, Leu580, Phe339, and Phe584 (C. D. Sibley, et al., J. Med. Chem. 63 (2020) 1178e1198). Further refinement of this SphK2 model may enable the use of alchemical methods for free energy calculations with congeneric ligands.

Example 5. In Vitro Biological Evaluation of Antitumor Activities

Recently, increasing evidence indicates that SphK2 is involved in numerous diseases such as cancer. Inhibition of SphK2 showed promising anti-tumor effects in multiple cancers such as non-small cell lung cancer, gastrointestinal cancer, breast cancer, and prostate cancer. It is proposed that SphK inhibitors can be used for treating malignant tumors such as glioblastoma, the most aggressive primary brain neoplasm with a median survival rate less than 1 year. Targeting on SphK2 may provide an efficient and effective approach to the treatment of tumor, particularly for glioblastoma.

Compound 7 (ABC294640) was reported as a well-known SphK2 selective inhibitor, and it is currently in phase II clinical trials for the treatment of pancreatic cancer and solid tumors through various mechanisms (V. Beljanski, et al., J. Pharmacol. Exp. Therapeut. 333 (2010) 454e464; J. W. Antoon, et al., Canc. Biol. Ther. 11 (2011) 678e689). To evaluate the anti-tumor activity of the SphK2 inhibitors, the antitumor activities of the compounds were compared with compound 7 using a human malignant glioblastoma tumor derived U-251 MG cell line. After 24 h incubation with 125 μM of each compound, it was found that compound 7 reduced viability of U-251 MG cells by approximately 50% as expected (FIG. 7A-7B) when compared with no treatment control (NTC) cells. Surprisingly, compounds 21a-b, and 25b tremendously decreased the viability of U-251 MG cells at 125 μM in 24 h, while compounds 21e, 25d, and 29a-b showed comparable reduction of viability of U-251 MG cells with compound 7.

Figure 8:
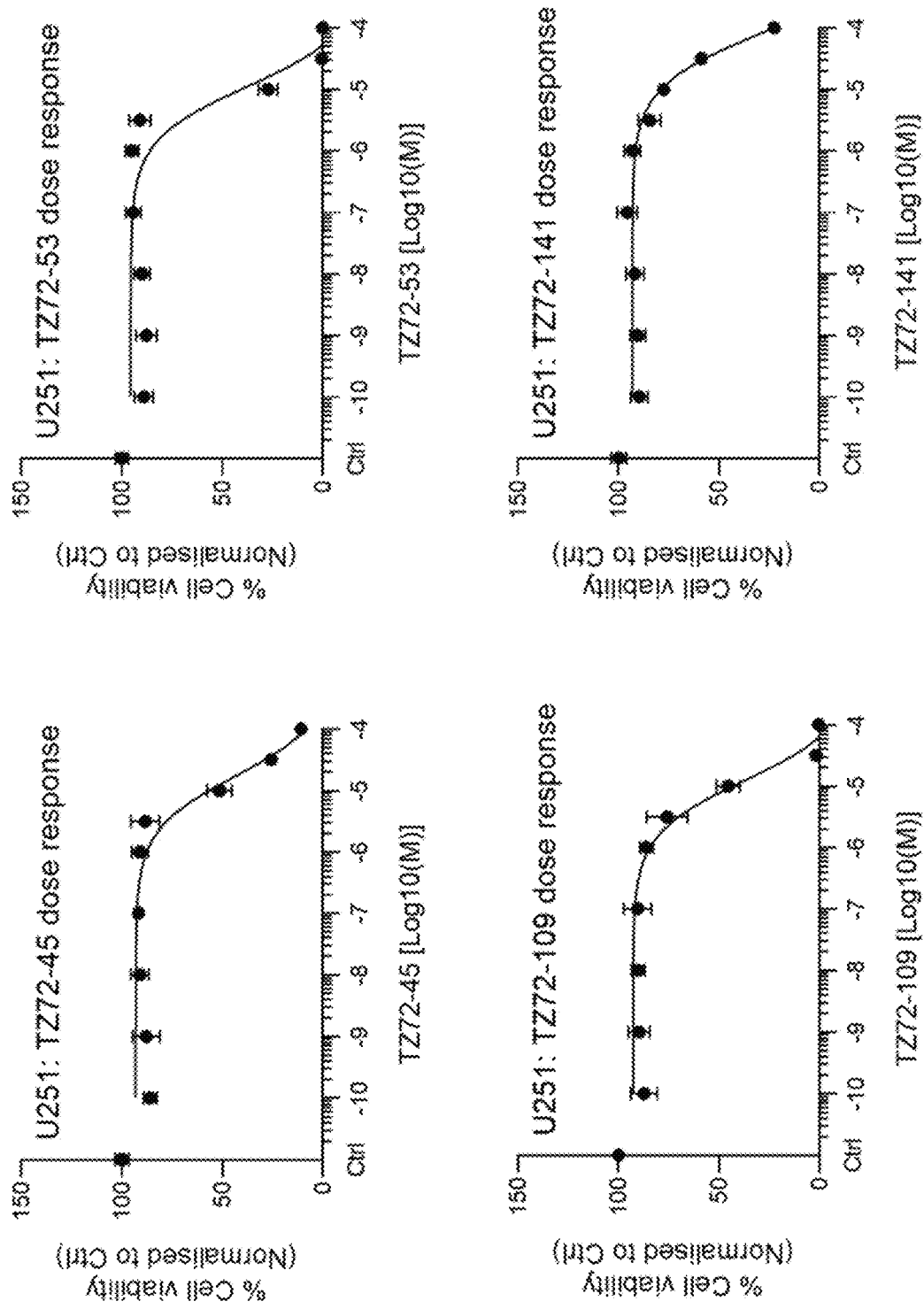
FIG. 8 depicts the effect of SphK2 inhibitors TZ72-45 (21a), TZ72-53 (21b), TZ72-109 (25b), and TZ72-141 (25d) on U-251 MG cell viability. Graphs represent percentage cell viability normalized to DMSO treated control (Ctrl) cells. Data expressed as mean±standard deviation (SD).

The anti-tumor activity of these inhibitors was further examined at different doses. U-251 MG cells were treated with increasing dose ($10^{-10}$ M to $10^{-4}$ M) of SphK2 inhibitors (TZ72-45 (21a), TZ72-53 (21b), TZ72-109 (25b), and TZ72-141 (25d)) in biological replicates of five for 72h, and dose response curves were generated (FIG. 8). $IC_{50}$ values were calculated by non-linear regression analysis of the dose-response curve and are shown in Table 4 below.

TABLE 4

SphK2 Inhibitor $IC_{50}$ Values

| SphK2 Inhibitor | $IC_{50}$ |
| --- | --- |
| TZ72-45 (21a) | 17.0 μM |
| TZ72-53 (21b) | 11.0 μM |
| TZ72-109 (25b) | 12.3 μM |
| TZ72-141 (25d) | 78.2 μM |

Figure 9:
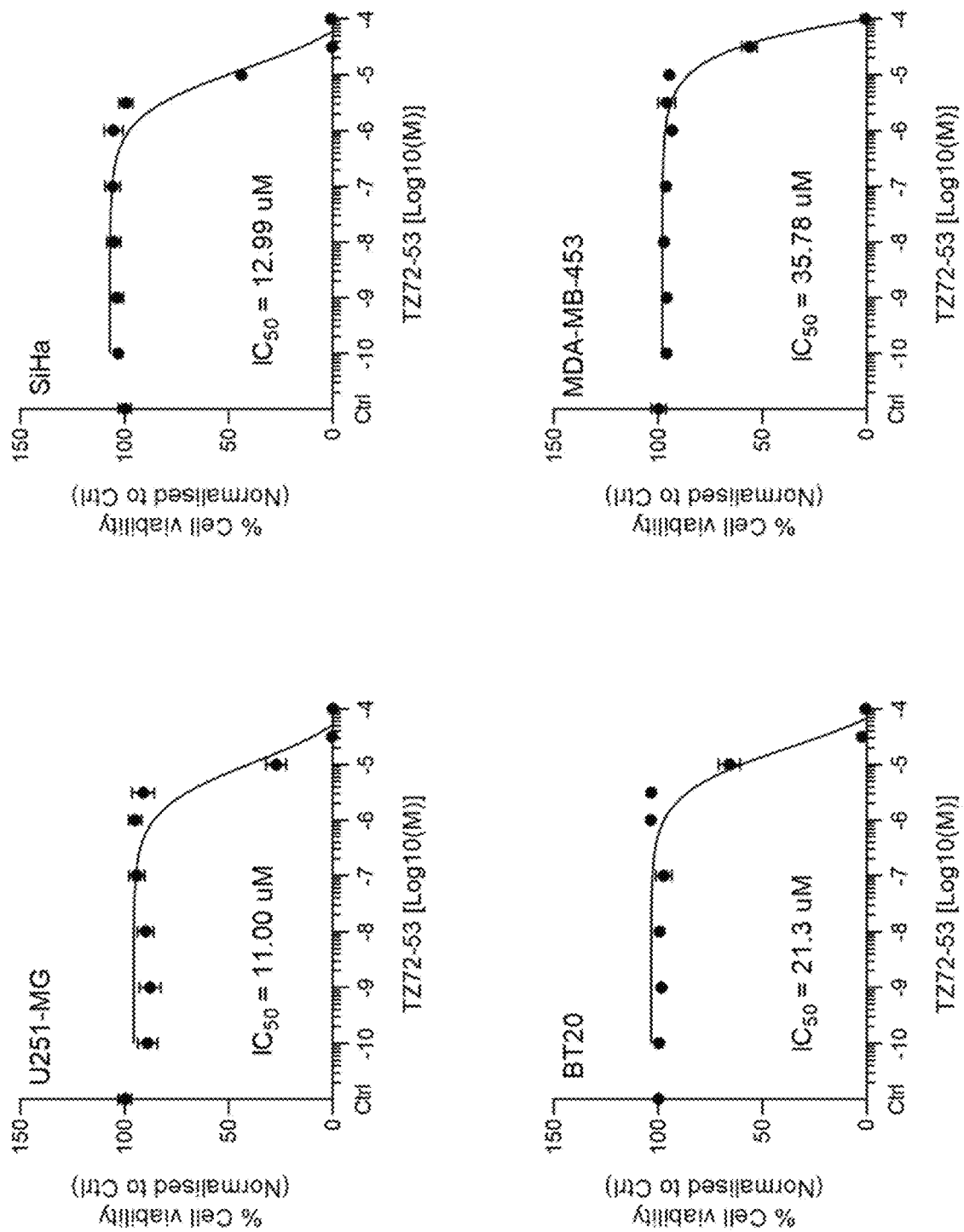
FIG. 9 depicts the effect of SphK2 inhibitor TZ72-53 (21b) on cell viability for U-251 MG cells, SiHa cells, BT20 cells, and MDA-MB-453 cells. Graphs represent percentage cell viability normalized to DMSO treated control (Ctrl) cells. Data expressed as mean±standard deviation (SD).

The anti-tumor activity of these inhibitors was also examined in different cell types. U-251 MG cells, SiHa cells, BT20 cells, and MDA-MB-453 cells were treated with increasing dose ($10^{-10}$ M to $10^{-4}$ M) of SphK2 inhibitor TZ72-53 (21b), and dose response curves were generated (FIG. 9). $IC_{50}$ values of 21b in the four different cell lines were calculated by non-linear regression analysis of the dose-response curve and are shown in Table 5 below.

TABLE 5

21b $IC_{50}$ Values in Different Cell Lines

| Cell Line | $IC_{50}$ |
| --- | --- |
| U-251 MG | 11.0 μM |
| SiHa | 12.99 μM |
| BT20 | 21.3 μM |
| MD-MB-453 | 35.78 μM |

These results suggest that the synthesized 1,2,3-triazole SphK2 inhibitors could act as anti-tumor agents. Whether the pathway of these compounds anti-tumor activity results only from direct SphK inhibition of SphK2 or another mechanism is not clear, further detailed investigations will help the clarification.

Example 6. Experimental

The following materials and methods were used in the rest of the Examples.
General All reagents and starting materials used in this study were obtained from commercial sources without any further purification. All dry reactions were conducted under a nitrogen atmosphere in oven dried glass apparatus using dry solvents. Yields refer to chromatographically, unless otherwise stated. Reactions were monitored by thin-layer chromatography (TLC) carried out on precoated glass plates of silica gel (0.25 mm) 60 $F_{254}$ from EMD Chemicals Inc. Visualization was accomplished with ultraviolet light (UV 254 nm), or by shaking the plate in a sealed jar containing silica gel and Iodine. Flash column chromatography was performed using Silia Flash® P60 40-63 mm (230-400 mesh) from Silicycle. Melting points were determined on a MEL-TEMP 3.0 apparatus. $^1$H NMR and $^{13}$C NMR spectra were recorded on Varian 400 MHz (operating at 400 MHz for $^1$H and 100 MHz for $^{13}$C NMR) spectrometer. Rotamers are denoted by an asterisk (*). Chemical shifts are reported in parts per million (ppm) and coupling constants J are given in Hz (Hertz). Chemical shifts are reported relative to TMS ($\delta$=0.0) as an internal standard. (Abbreviations used in spectra: s=singlet, d=doublet, t=triplet, q=quartet, m=multiplet, br=broad, dd=double of doublets, dt=doublet of triplets, td=triplet of doublets, qd=quartet of doublets). High resolution mass spectra (HRMS) [ESI]$^+$ were recorded on a Bruker MaXis 4G Q-TOF mass spectrometer with electrospray ionization source.

CHEMISTRY

General procedure A: coupling of amide-oxime derivatives with (S)-2-(1-(tert-butoxycarbonyl)pyrrolidin-2-yl)acetic acid/N-(tert-butoxycarbonyl)-L-proline To a solution of (S)-2-(1-(tert-butoxycarbonyl)pyrrolidin-2-yl) acetic acid/N-(tert-butoxycarbonyl)-L-proline (1.1 equiv) in DMF (10 mL) was added DIPEA (1.8 equiv) and followed by addition of HCTU (1.5 equiv). The reaction mixture was stirred for 0.5 h followed by adding amidoxime (1.0 equiv). The reaction mixture was stirred for 1 h at room temperature, then stirred at 100° C. oil-bath for 8-10 h. The reaction progress was monitored by TLC. The solution was partitioned between EtOAc and LiBr aqueous solution. The aqueous solution was washed with EtOAc (3×10 mL), and the combined organic layers were washed with brine, dried over $Na_2SO_4$, filtered, and concentrated via vacuum. The resulting residue was purified by silica gel column chromatography.

General Procedure B: Synthesis of 1,2,3-Triazole Derivatives

To a vigorously stirred solution of the azide (1 equiv) in DCM (5 mL) was added various terminal alkynes (1.1 equiv). The reaction was initiated by the addition of a solution of $CuSO_4 \cdot 5H_2O$ (0.01 equiv) and sodium ascorbate (0.1 equiv) in distilled water (5 mL). The coloured suspension that formed was stirred at room temperature for 10-12 h. The reaction progress was monitored by TLC. After completion of the reaction, the resulting mixture was diluted with $CH_2Cl_2$ and then washed with brine. The combined organic extracts were dried over anhydrous $Na_2SO_4$ and then concentrated under reduced pressure to afford crude product, which was purified by silica gel column chromatography to obtain pure 1,2,3-triazoles.

General procedure C: deprotection of t-Boc protecting groups with TFA and guanylation of amines To a solution of azole based t-Boc-protected intermediates (1.0 equiv) in $CH_2Cl_2$ (5 mL) was added a TFA (6.0 equiv) in $CH_2Cl_2$ (5 mL). The reaction mixture was then stirred at rt for 4-6 h, and monitored via TLC. At this time, TLC showed complete conversion of the starting material. The organic solvent was removed under reduced pressure. The residue was then dissolved in $CH_3CN$ (10 mL). Diisopropylethylamine (10 equiv) and (Z)-tert-butyl (((tert-butoxycarbonyl)imino)($^1$H-pyrazol-1-yl)methyl)carbamate (1.1 equiv) were added to the above solution, and the resulting reaction mixture was stirred at 50° C. for 8-10 h, and monitored via TLC. Once the starting material was consumed, the reaction was cooled to room temperature, and the solvent was removed under reduced pressure to afford the crude residue. The resulting residue was purified by silica gel column chromatography with 40-50% EtOAc in hexane to afford the desired 1,2,3-triazole based guanylated derivatives.

General Procedure D: Deprotection of t-Boc Protecting Groups with HCl

To a solution of N-Boc-protected compounds (1.0 equiv) in methanol (1 mL) was then added 4 N hydrochloric acid (HCl) solution in dioxane (1 mL). The resulting reaction mixture was stirred for 2-3 h and monitored via TLC. Once the starting material was consumed, and the solvent was removed under reduced pressure to get the residue. The resulting residue was triturated with diethyl ether to yield the corresponding free amine hydrochloride salt.

General Procedure E: Conversion of Nitriles to Amidines

To a solution of a nitrile (1.0 eq.) in MeOH (0.10 M) was added a 0.5 M solution of sodium methoxide in MeOH (0.50 eq.) at rt and then heated to 50° C. for 24 h. The intermediate imidate was detectable by TLC; however, being in equilibrium with the nitrile, full conversion does not occur. Ammonium chloride (4.0 eq.) was then added in one portion at that temperature and allowed to react until the imidate was completely consumed by TLC analysis. The reaction was then cooled to rt and evacuated to dryness to yield a crude solid. The solid was dissolved in minimum amount of water in order to remove excess ammonium chloride, and the solid was again evacuated to dryness. The crude solid material was then recrystallized in $Et_2O$ and DCM to yield the pure amidine hydrochloride salt. The yields varied greatly depending upon substrate, because amidine formation is dependent upon the equilibrium ratio between nitrile and imidate established under the sodium methoxide conditions.

4-(Azidomethyl)benzonitrile (16)

To a round-bottom flask equipped with a stir bar was added 4-(hydroxymethyl)benzonitrile (5.0 g, 37.55 mmol), diphenyl phosphoryl azide (9.68 mL, 45.06 mmol), and toluene (25 mL). The mixture was cooled to 0° C. before adding 1,8-diazabicyclo [5.4.0] undec-7-ene (6.72 mL, 45.06 mmol) dropwise. The reaction was warmed to room temperature slowly and continued to stir for overnight. The reaction progress was monitored by TLC. After completion of the reaction, the resulting mixture was diluted with water (30 mL) and extracted with ethyl acetate (30 mL). The ethyl acetate layer was washed with 1 M HCl, saturated brine and dried over anhydrous $Na_2SO_4$. The organic solvent was removed under reduced pressure. The crude residue was purified on a silica gel column chromatography, eluted with 10% EtOAc in hexane to afford the desired compound 16 (5.52 g, 93% yield) as a colorless solid. $^1$H NMR (400 MHz, $CDCl_3$) δ 7.65 (d, J 8.3 Hz, 2H), 7.41 (d, J 8.3 Hz, 2H), 4.42 (s, 2H).

4-(Azidomethyl)-N0-hydroxybenzimidamide (17)

To a stirred suspension of $NH_2OH$—HCl (4.39 g, 63.22 mmol) and $NaHCO_3$ (10.62 g, 126.44 mmol) in $CH_3OH$ (50 mL), a solution of 16 (5.0 g, 31.61 mmol) in $CH_3OH$ (10 mL) was gradually added. The reaction was refluxed and stirred in a pre-heated 75° C. oil-bath for 8 h. The reaction progress was monitored by TLC. After completion of the reaction, it was cooled to room temperature, and the precipitate was filtered off and washed with methanol. The filtrate was concentrated in vacuo without further purification to afford 17 (5.50 g, 91% yield) as a white solid. $^1$H NMR (400 MHz, DMSO-$d_6$) δ 9.68 (s, 1H), 7.71 (d, J=8.2 Hz, 2H), 7.37 (d, J=8.2 Hz, 2H), 5.83 (s, 2H), 4.46 (s, 2H).

(S)-tert-Butyl-2-((3-(4-(azidomethyl)phenyl)-1,2,4-oxadiazol-5-yl)methyl)pyrrolidine-1-carboxylate (18)

Synthesized by general procedure A: Yield: 56%; Pale yellow color solid; $^1$H NMR (400 MHz, $CDCl_3$) δ 8.08 (d, J=8.2 Hz, 2H), 7.41 (d, J=8.0 Hz, 2H), 4.40 (s, 2H), 4.28 (d, J=24.9 Hz, 1H), 3.45-3.28 (m, 3H), 3.15-2.98 (m, 1H), 2.12-2.03 (m, 1H), 1.90-1.78 (m, 3H), 1.45 (s, 9H).

(S)-tert-Butyl-2-((3-(4-((4-phenyl-1H-1,2,3-triazol-1-yl)methyl)phenyl)-1,2,4-oxadiazol-5-yl)methyl)pyrrolidine-1-carboxylate (19a)

Synthesized by general procedure B: Yield: 81%; White solid; $^1$H NMR (400 MHz, $CDCl_3$) δ 8.08 (d, J=8.1 Hz, 2H), 7.79 (d, J=7.4 Hz, 2H), 7.69 (s, 1H), 7.42-7.36 (m, 4H), 7.30 (t, J=7.3 Hz, 1H), 5.62 (s, 2H), 4.27 (d, J=31.0 Hz, 1H), 3.43-3.27 (m, 3H), 3.15-2.97 (m, 1H), 2.10-2.03 (m, 1H), 1.91-1.77 (m, 3H), 1.44 (s, 9H).

(S)-tert-Butyl-2-((3-(4-((4-(4-(trifluoromethyl)phenyl)-1H-1,2,3-triazol-1-yl)methyl)phenyl)-1,2,4-oxadiazol-5-yl)methyl)pyrrolidine-1-carboxylate (19b)

Synthesized by general procedure B: Yield: 45%; White solid; $^1$H NMR (400 MHz, $CDCl_3$) δ 8.09 (d, J=8.2 Hz, 2H), 7.90 (d, J=8.1 Hz, 2H), 7.76 (s, 1H), 7.64 (d, J=8.2 Hz, 2H), 7.40 (d, J=8.0 Hz, 2H), 5.64 (s, 2H), 4.27 (d, J=31.4 Hz, 1H), 3.45-3.27 (m, 3H), 3.12-2.98 (m, 1H), 2.09-1.99 (m, 1H), 1.89-1.77 (m, 3H), 1.44 (s, 9H).

(S)-tert-Butyl-2-((3-(4-((4-(pyridin-2-yl)-1H-1,2,3-triazol-1-yl)methyl)phenyl)-1,2,4-oxadiazol-5-yl)methyl)pyrrolidine-1-carboxylate (19c)

Synthesized by general procedure B: Yield: 78%; White solid; $^1$H NMR (400 MHz, $CDCl_3$) δ 8.51 (d, J=4.8 Hz, 1H), 8.15 (d, J=7.9 Hz, 1H), 8.10-8.03 (m, 3H), 7.74 (td, J=7.6, 1.2 Hz, 1H), 7.40 (d, J=8.0 Hz, 2H), 7.19 (dd, J=6.6, 5.1 Hz, 1H), 5.62 (s, 2H), 4.26 (d, J=29.4 Hz, 1H), 3.42-3.37 (m, 3H), 3.13-2.96 (m, 1H), 2.09-2.03 (m, 1H), 1.90-1.75 (m, 3H), 1.43 (s, 9H).

(S)-tert-Butyl-2-((3-(4-((4-butyl-1H-1,2,3-triazol-1-yl)methyl)phenyl)-1,2,4-oxadiazol-5-yl)methyl)pyrrolidine-1-carboxylate (19d)

Synthesized by general procedure B: Yield: 85%; White solid; $^1$H NMR (400 MHz, $CDCl_3$) δ 8.05 (d, J=8.1 Hz, 2H), 7.32 (d, J=8.0 Hz, 2H), 7.19 (s, 1H), 5.53 (s, 2H), 4.26 (d, J=33.0 Hz, 1H), 3.45-3.26 (m, 3H), 3.12-3.00 (m, 1H), 2.68 (t, J=7.7 Hz, 2H), 2.10-2.05 (m, 1H), 1.92-1.76 (m, 3H), 1.65-1.57 (m, 2H), 1.44 (s, 9H), 1.37-1.31 (q, 2H), 0.89 (t, J=7.3 Hz, 3H).

(S)-tert-Butyl-2-((3-(4-((4-(4-methoxyphenyl)-1H-1,2,3-triazol-1-yl)methyl)phenyl)-1,2,4-oxadiazol-5-yl)methyl)pyrrolidine-1-carboxylate (19e)

Synthesized by general procedure B: Yield: 57%; White solid; $^1$H NMR (400 MHz, $CDCl_3$) δ 8.11 (d, J=8.2 Hz, 2H), 7.75 (d, J=8.8 Hz, 2H), 7.64 (s, 1H), 7.42 (d, J=8.0 Hz, 2H), 6.96 (d, J=8.8 Hz, 2H), 5.64 (s, 2H), 4.31 (d, J=36.5 Hz, 1H), 3.85 (s, 3H), 3.46-3.32 (m, 3H), 3.16-3.02 (m, 1H), 2.13-2.04 (m, 1H), 1.93-1.78 (m, 3H), 1.48 (s, 9H).

(S)-tert-Butyl-2-((3-(4-((4-cyclopropyl-1H-1,2,3-triazol-1-yl)methyl)phenyl)-1,2,4-oxadiazol-5-yl)methyl)pyrrolidine-1-carboxylate (19f)

Synthesized by general procedure B: Yield: 89%; White solid; $^1$H NMR (400 MHz, $CDCl_3$) δ 8.11 (d, J=8.1 Hz, 2H), 7.38 (d, J=8.0 Hz, 2H), 7.22 (s, 1H), 5.57 (s, 2H), 4.33 (d, J=27.4 Hz, 1H), 3.53-3.34 (m, 3H), 3.23-3.04 (m, 1H), 2.14-2.11 (m, 1H), 2.00-1.88 (m, 4H), 1.50 (s, 9H), 1.02-0.94 (m, 2H), 0.89-0.85 (m, 2H).

(S)-tert-Butyl-2-((3-(4-((4-(1-methyl-1H-pyrazol-4-yl)-1H-1,2,3-triazol-1-yl)methyl)phenyl)-1,2,4-oxadiazol-5-yl)methyl)pyrrolidine-1-carboxylate (19g)

Synthesized by general procedure B: Yield: 51%; White solid; $^1$H NMR (400 MHz, CDCl$_3$) δ 8.11 (d, J=7.9 Hz, 2H), 7.80 (s, 1H), 7.72 (s, 1H), 7.51 (s, 1H), 7.41 (d, J=7.7 Hz, 2H), 5.62 (s, 2H), 4.30 (d, J=27.6 Hz, 1H), 3.95 (s, 3H), 3.47-3.31 (m, 3H), 3.14-3.00 (m, 1H), 2.11-2.02 (m, 1H), 1.94-1.80 (br m, 3H), 1.47 (s, 9H).

(S)-tert-Butyl-(((tert-butoxycarbonyl)imino)(2-((3-(4-((4-phenyl-1H-1,2,3-triazol-1-yl)methyl)phenyl)-1,2,4-oxadiazol-5-yl)methyl)pyrrolidin-1-yl)methyl)carbamate (20a)

Synthesized by general procedure C: Yield: 51%; White solid; $^1$H NMR (400 MHz, CDCl$_3$) δ 10.27 (s, 1H), 8.10 (d, J=8.0 Hz, 2H), 7.79 (d, J=7.6 Hz, 2H), 7.67 (s, 1H), 7.39 (dd, J=7.4, 5.1 Hz, 4H), 7.30 (t, J=7.3 Hz, 1H), 5.62 (s, 2H), 4.77-4.73 (m, 1H), 3.66-3.59 (m, 2H), 3.50-3.41 (m, 1H), 3.19-3.13 (m, 1H), 2.27-2.20 (m, 1H), 1.91-1.87 (m, 1H), 1.82-1.73 (m, 2H), 1.44 (s, 18H).

(S)-tert-Butyl-(((tert-butoxycarbonyl)imino)(2-((3-(4-((4-(4-(trifluoromethyl)phenyl)-1H-1,2,3-triazol-1-yl)methyl)phenyl)-1,2,4-oxadiazol-5-yl)methyl)pyrrolidin-1-yl)methyl)carbamate (20b)

Synthesized by general procedure C: Yield: 60%; White solid; $^1$H NMR (400 MHz, CDCl$_3$) δ 10.38 (s, 1H), 8.19 (d, J=7.8 Hz, 2H), 7.98 (d, J=7.9 Hz, 2H), 7.83 (s, 1H), 7.72 (d, J=8.0 Hz, 2H), 7.48 (d, J=7.9 Hz, 2H), 5.72 (s, 2H), 4.85-4.82 (m, 1H), 3.71 (dd, J=17.2, 7.9 Hz, 2H), 3.59-3.49 (m, 1H), 3.24 (dd, J=14.4, 8.5 Hz, 1H), 2.34-2.27 (m, 1H), 1.98-1.94 (m, 1H), 1.90-1.81 (m, 2H), 1.52 (s, 18H).

(S)-tert-Butyl-(((tert-butoxycarbonyl)imino)(2-((3-(4-((4-(pyridin-2-yl)-1H-1,2,3-triazol-1-yl)methyl)phenyl)-1,2,4-oxadiazol-5-yl)methyl)pyrrolidin-1-yl)methyl)carbamate (20c)

Synthesized by general procedure C: Yield: 25%; White solid; $^1$H NMR (400 MHz, CDCl$_3$) δ 10.36 (s, 1H), 8.59 (d, J=4.9 Hz, 1H), 8.23 (d, J=7.9 Hz, 1H), 8.19-8.11 (m, 3H), 7.82 (t, J=7.6 Hz, 1H), 7.47 (d, J=8.0 Hz, 2H), 7.30-7.24 (m, 1H), 5.70 (s, 2H), 4.83-4.79 (m, 1H), 3.74-3.66 (m, 2H), 3.57-3.47 (m, 1H), 3.24 (dd, J=17.7, 8.2 Hz, 1H), 2.33-2.26 (m, 1H), 2.03-1.93 (m, 1H), 1.92-1.79 (m, 2H), 1.51 (d, J=5.0 Hz, 18H).

(S)-tert-Butyl-(((tert-butoxycarbonyl)imino)(2-((3-(4-((4-butyl-1H-1,2,3-triazol-1-yl)methyl)phenyl)-1,2,4-oxadiazol-5-yl)methyl)pyrrolidin-1-yl)methyl)carbamate (20d)

Synthesized by general procedure C: Yield: 33%; White solid; $^1$H NMR (400 MHz, CDCl$_3$) δ 10.34 (s, 1H), 8.12 (d, J=8.0 Hz, 2H), 7.37 (d, J=8.1 Hz, 2H), 7.24 (s, 1H), 5.58 (s, 2H), 4.82-4.76 (m, 1H), 3.68 (dd, J=16.9, 9.6 Hz, 2H), 3.55-3.49 (m, 1H), 3.21 (dd, J=14.7, 8.0 Hz, 1H), 2.74 (t, J=7.7 Hz, 2H), 2.33-2.26 (m, 1H), 2.01-1.92 (m, 1H), 1.88-1.81 (m, 2H), 1.70-1.64 (m, 2H), 1.50 (d, J=9.0 Hz, 18H), 1.40 (dd, J=14.9, 7.4 Hz, 2H), 0.95 (t, J=7.3 Hz, 3H).

(S)-tert-Butyl-(((tert-butoxycarbonyl)imino)(2-((3-(4-((4-(4-methoxyphenyl)-1H-1,2,3-triazol-1-yl)methyl)phenyl)-1,2,4-oxadiazol-5-yl)methyl)pyrrolidin-1-yl)methyl)carbamate (20e)

Synthesized by general procedure C: Yield: 22%; White solid; $^1$H NMR (400 MHz, CDCl$_3$) δ 10.32 (s, 1H), 8.13 (d, J=8.0 Hz, 2H), 7.75 (d, J=8.7 Hz, 2H), 7.63 (s, 1H), 7.42 (d, J=8.0 Hz, 2H), 6.96 (d, J=8.7 Hz, 2H), 5.64 (s, 2H), 4.85-4.74 (m, 1H), 3.85 (s, 3H), 3.72-3.62 (m, 2H), 3.20 (dd, J=15.0, 8.2 Hz, 1H), 2.31-2.25 (m, 1H), 1.99-1.75 (m, 4H), 1.48 (s, 18H).

(S)-tert-Butyl-(((tert-butoxycarbonyl)imino)(2-((3-(4-((4-cyclopropyl-1H-1,2,3-triazol-1-yl)methyl)phenyl)-1,2,4-oxadiazol-5-yl)methyl)pyrrolidin-1-yl)methyl)carbamate (20f)

Synthesized by general procedure C: Yield: 25%; White solid; $^1$H NMR (400 MHz, CDCl$_3$) δ 10.34 (s, 1H), 8.12 (d, J=8.0 Hz, 2H), 7.37 (d, J=8.0 Hz, 2H), 7.19 (s, 1H), 5.55 (s, 2H), 4.83-4.77 (m, 1H), 3.76-3.63 (m, 2H), 3.59-3.47 (m, 1H), 3.21 (dd, J=14.7, 7.5 Hz, 1H), 2.34-2.23 (m, 1H), 1.99-1.92 (m, 2H), 1.88-1.80 (m, 2H), 1.50 (s, 18H), 0.98-0.94 (m, 2H), 0.89-0.83 (m, 2H).

(S)-tert-Butyl-(((tert-butoxycarbonyl)imino)(2-((3-(4-((4-(1-methyl-1H-pyrazol-4-yl)-1H-1,2,3-triazol-1-yl)methyl)phenyl)-1,2,4-oxadiazol-5-yl)methyl)pyrrolidin-1-yl)methyl)carbamate (20g)

Synthesized by general procedure C: Yield: 19%; White solid; $^1$H NMR (400 MHz, CDCl$_3$) δ 10.34 (s, 1H), 8.14 (d, J=8.0 Hz, 2H), 7.82 (s, 1H), 7.74 (s, 1H), 7.53 (s, 1H), 7.42 (d, J=8.0 Hz, 2H), 5.64 (s, 2H), 4.86-4.76 (m, 1H), 3.97 (s, 3H), 3.74-3.64 (m, 2H), 3.58-3.47 (m, 1H), 3.23-3.16 (m, 1H), 2.34-2.24 (m, 1H), 1.99-1.82 (m, 3H), 1.53-1.45 (m, 18H).

(S)-2-((3-(4-((4-Phenyl-1H-1,2,3-triazol-1-yl)methyl)phenyl)-1,2,4-oxadiazol-5yl)methyl)pyrrolidine-1-carboximidamide hydrochloride (21a)

Synthesized by general procedure D: Yield: 85%; White solid; $^1$H NMR (400 MHz, CD$_3$OD) δ 8.56 (s, 1H), 8.11 (d, J=8.2 Hz, 2H), 7.82 (d, J=7.3 Hz, 2H), 7.57 (d, J=8.2 Hz, 2H), 7.46 (t, J=7.4 Hz, 2H), 7.39 (t, J=7.4 Hz, 1H), 5.79 (s, 2H), 4.53 (q, J=7.5 Hz, 1H), 3.76-3.66 (m, 1H), 3.60-3.41 (m, 3H), 2.33-2.22 (m, 1H), 2.16-2.01 (m, 3H); $^{13}$C NMR (101 MHz, CD$_3$OD×DMSO-d$_6$) δ 178.45, 168.96, 156.12, 148.84, 140.66, 131.88, 130.15, 129.91, 129.42, 128.96, 127.87, 126.68, 122.73, 56.86, 54.34, 48.83, 31.55, 30.08, 23.53; HRMS (ESI) m/z [M×H]$^+$ calcd. for C$_{23}$H$_{25}$N$_8$O 429.2146, found 429.2149.

(S)-2-((3-(4-((4-(4-(Trifluoromethyl)phenyl)-1H-1,2,3-triazol-1-yl)methyl)phenyl)-1,2,4-oxadiazol-5-yl)methyl)-pyrrolidine-1-carboximidamide hydrochloride (21b)

Synthesized by general procedure D: Yield: 89%; White solid; $^1$H NMR (400 MHz, CD$_3$OD) δ 8.57 (s, 1H), 8.09 (d, J=8.0 Hz, 2H), 8.02 (d, J=8.1 Hz, 2H), 7.73 (d, J=8.1 Hz, 2H), 7.54 (d, J=8.1 Hz, 2H), 5.77 (s, 2H), 4.57-4.49 (m, 1H), 3.68-3.42 (m, 3H), 3.32 (s, 1H), 2.31-2.23 (m, 1H), 2.16-1.98 (m, 3H); $^{13}$C NMR (101 MHz, DMSO-$d_6$) δ 177.70, 167.58, 155.08, 145.73, 139.68, 134.97, 133.69, 129.25, 128.64*, 128.32*, 127.95, 126.39, 126.35, 126.31, 126.14, 126.00*, 123.57, 123.30*, 105.42, 55.21, 53.16, 47.88, 30.39, 29.24, 22.49; HRMS (ESI) m/z [M×H]$^+$ calcd. for $C_{24}H_{24}F_3N_8O$ 497.2015, found 497.2014.

(S)-2-((3-(4-((4-(Pyridin-2-yl)-1H-1,2,3-triazol-1-yl)methyl)phenyl)-1,2,4-oxadiazol-5-yl)methyl)pyrrolidine-1-carboximidamide hydrochloride (21c)

Synthesized by general procedure D: Yield: 78%; White solid; $^1$H NMR (400 MHz, CD$_3$OD) δ 9.07 (s, 1H), 8.78 (d, J=5.4 Hz, 1H), 8.65 (t, J=7.3 Hz, 1H), 8.48 (d, J=8.2 Hz, 1H), 8.11 (d, J=8.3 Hz, 2H), 7.99 (t, J=6.8 Hz, 1H), 7.60 (d, J=8.2 Hz, 2H), 5.87 (s, 2H), 4.56-4.51 (m, 1H), 3.57-3.43 (m, 2H), 3.34 (d, J=5.0 Hz, 2H), 2.31-2.24 (m, 1H), 2.18-1.97 (m, 3H); $^{13}$C NMR (101 MHz, DMSO-$d_6$) δ 177.72, 167.56, 155.11, 146.54*, 146.09, 142.54*, 139.44, 129.35, 129.30*, 128.06*, 127.96, 126.47, 125.98, 124.91, 122.03, 55.20, 53.28, 47.88, 31.73*, 30.39, 29.25, 22.50; HRMS (ESI) m/z [M×H]$^+$ calcd. for $C_{22}H_{24}N_9O$ 430.2098, found 430.2100.

(S)-2-((3-(4-((4-Butyl-1H-1,2,3-triazol-1-yl)methyl)phenyl)-1,2,4-oxadiazol-5-yl)methyl)pyrrolidine-1-carboximidamide hydrochloride (21d)

Synthesized by general procedure D: Yield: 89%; White solid; $^1$H NMR (400 MHz, CD$_3$OD) δ 8.36 (s, 1H), 8.12 (d, J=8.1 Hz, 2H), 7.58 (d, J=8.1 Hz, 2H), 5.83 (s, 2H), 4.59-4.48 (m, 1H), 3.60-3.41 (m, 3H), 3.34 (d, J=3.9 Hz, 1H), 2.83 (t, J=7.7 Hz, 2H), 2.34-2.21 (m, 1H), 2.14-2.01 (m, 3H), 1.75-1.65 (m, 2H), 1.47-1.35 (m, 2H), 0.96 (t, J=7.4 Hz, 3H); $^{13}$C NMR (101 MHz, DMSO-$d_6$) δ 177.67, 167.59, 155.07, 147.60, 140.14, 129.07, 127.85, 126.21, 122.78, 55.21, 52.73, 47.88, 31.46, 30.39, 29.23, 25.01, 22.49*, 22.09, 14.11; HRMS (ESI) m/z [M×H]$^+$ calcd. for $C_{21}H_{29}N_8O$ 409.2459, found 409.2458.

(S)-2-((3-(4-((4-(4-Methoxyphenyl)-1H-1,2,3-triazol-1-yl)methyl)phenyl)-1,2,4-oxadiazol-5-yl)methyl)pyrrolidine-1-carboximidamide hydrochloride (21e)

Synthesized by general procedure D: Yield: 91%; White solid; $^1$H NMR (400 MHz, CD$_3$OD) δ 8.41 (s, 1H), 8.10 (d, J=8.1 Hz, 2H), 7.74 (d, J=8.6 Hz, 2H), 7.54 (d, J=8.1 Hz, 2H), 7.01 (d, J=8.6 Hz, 2H), 5.76 (s, 2H), 4.52 (d, J=6.8 Hz, 1H), 3.83 (s, 3H), 3.66 (d, J=3.7 Hz, 1H), 3.58-3.41 (m, 2H), 3.32 (d, J=1.6 Hz, 1H), 2.32-2.22 (m, 1H), 2.15-1.99 (m, 3H); $^{13}$C NMR (101 MHz, DMSO-$d_6$) δ 177.69, 167.60, 159.47, 155.06, 147.06, 139.98, 129.14, 127.91, 126.96, 126.29, 123.60, 121.29, 114.74, 55.59, 55.21, 52.99, 47.87, 30.39, 29.24, 22.49; HRMS (ESI) m/z [M×H]$^+$ calcd. for $C_{24}H_{27}N_8O_2$ 459.2251, found 459.2251.

(S)-2-((3-(4-((4-Cyclopropyl-1H-1,2,3-triazol-1-yl)methyl)phenyl)-1,2,4-oxadiazol-5-yl)methyl)pyrrolidine-1-carboximidamide hydrochloride (21f)

Synthesized by general procedure D: Yield: 75%; White solid; $^1$H NMR (400 MHz, CD$_3$OD) δ 8.29 (s, 1H), 8.11 (d, J=8.0 Hz, 2H), 7.57 (d, J=8.1 Hz, 2H), 5.79 (s, 2H), 4.58-4.51 (m, 1H), 3.76-3.63 (m, 1H), 3.63-3.43 (m, 3H), 2.34-2.23 (m, 1H), 2.17-2.01 (m, 4H), 1.18-1.13 (m, 2H), 0.92 (q, J=5.2 Hz, 2H); $^{13}$C NMR (101 MHz, DMSO-$d_6$) δ 177.68, 167.59, 155.07, 149.69, 140.09, 129.07, 127.85, 126.21, 121.63, 55.21, 52.75, 47.88, 30.39, 29.24, 22.49, 8.12, 6.93; HRMS (ESI) m/z [M×H]$^+$ calcd. for $C_{20}H_{25}N_8O$ 393.2146, found 393.2141.

(S)-2-((3-(4-((4-(1-Methyl-1H-pyrazol-4-yl)-1H-1,2,3-triazol-1-yl)methyl)phenyl)-1,2,4-oxadiazol-5-yl)methyl)pyrrolidine-1-carboximidamide hydrochloride (21g)

Synthesized by general procedure D: Yield: 71%; White solid; $^1$H NMR (400 MHz, CD$_3$OD) δ 8.50 (d, J=1.6 Hz, 1H), 8.34 (d, J=2.3 Hz, 2H), 8.20 (s, 1H), 8.11 (d, J=8.1 Hz, 2H), 8.04 (s, 1H), 7.58 (d, J=8.1 Hz, 2H), 6.86 (s, 1H), 5.81 (s, 2H), 4.53 (q, J=8.1 Hz, 1H), 4.01 (s, 3H), 3.66 (s, 1H), 3.59-3.41 (m, 2H), 3.34 (d, J=5.3 Hz, 1H), 2.33-2.24 (dt, J=18.3, 7.3 Hz, 1H), 2.17-1.98 (m, 3H); $^{13}$C NMR (101 MHz, CD$_3$OD+DMSO-$d_6$) δ 177.50, 167.58, 154.68, 140.72, 139.79, 136.48, 133.77, 128.98, 128.32, 127.79, 126.36, 120.68, 112.88, 106.25, 55.31, 52.85, 47.79, 38.68, 30.33, 29.05, 22.38; HRMS (ESI) m/z [M×H]$^+$ calcd. for $C_{21}H_{25}N_{10}O$ 433.2207, found 433.2203.

(S)-tert-Butyl-2-((3-(4-(azidomethyl)phenyl)-1,2,4-oxadiazol-5-yl)pyrrolidine-1-carboxylate (22)

Synthesized by general procedure A: Yield: 89%; Liquid; $^1$H NMR (400 MHz, CDCl$_3$) δ 8.08 (d, J=7.8 Hz, 2H), 7.42 (d, J=7.9 Hz, 2H), 5.21-5.03 (m, 1H), 4.40 (s, 2H), 3.75-3.61 (m, 1H), 3.58-3.47 (m, 1H), 2.44-2.29 (m, 1H), 2.16-2.09 (m, 2H), 2.01-1.94 (m, 1H), 1.44 (s, 3H), 1.28 (s, 6H).

(S)-tert-Butyl-2-((3-(4-((4-phenyl-1H-1,2,3-triazol-1-yl)methyl)phenyl)-1,2,4-oxadiazol-5-yl)pyrrolidine-1-carboxylate (23a)

Synthesized by general procedure B: Yield: 78%; White solid; $^1$H NMR (400 MHz, CDCl$_3$) δ 8.08 (d, J=7.9 Hz, 2H), 7.79 (d, J=7.7 Hz, 2H), 7.69 (d, J=8.7 Hz, 1H), 7.39 (t, J=7.6 Hz, 4H), 7.30 (t, J=7.3 Hz, 1H), 5.62 (s, 2H), 5.21-5.02 (m, 1H), 3.72-3.63 (m, 1H), 3.57-3.44 (m, 1H), 2.42-2.33 (m, 1H), 2.19-2.06 (m, 2H), 2.00-1.95 (m, 1H), 1.44 (s, 3H), 1.27 (s, 6H).

(S)-tert-Butyl-2-((3-(4-((4-(4-(trifluoromethyl)phenyl)-1H-1,2,3-triazol-1-yl)methyl)phenyl)-1,2,4-oxadiazol-5-yl)pyrrolidine-1-carboxylate (23b)

Synthesized by general procedure B: Yield: 83%; White solid; $^1$H NMR (400 MHz, CDCl$_3$) δ 8.03 (d, J=7.4 Hz, 2H), 7.85 (d, J=7.9 Hz, 2H), 7.74 (s, 1H), 7.58 (d, J=7.4 Hz, 2H), 7.34 (dd, J=14.0, 7.9 Hz, 2H), 5.58 (s, 2H), 5.13-4.98 (m, 1H), 3.68-3.55 (m, 1H), 3.49-3.41 (m, 1H), 2.40-2.25 (m, 1H), 2.13-1.99 (m, 2H), 1.96-1.91 (m, 1H), 1.38 (s, 4H), 1.21 (s, 5H).

(S)-tert-Butyl-2-((3-(4-((4-(pyridin-2-yl)-1H-1,2,3-triazol-1-yl)methyl)phenyl)-1,2,4-oxadiazol-5-yl)pyrrolidine-1-carboxylate (23c)

Synthesized by general procedure B: Yield: 80%; White solid; $^1$H NMR (400 MHz, CDCl$_3$) δ 8.52 (d, J=4.8 Hz, 1H), 8.16 (d, J=7.8 Hz, 1H), 8.08 (d, J=5.2 Hz, 2H), 7.83-7.71 (m, 1H), 7.42 (d, J=8.1 Hz, 2H), 7.20 (dd, J=6.9, 5.4 Hz, 1H), 5.63 (s, 2H), 5.21-5.00 (m, 1H), 3.77-3.62 (m, 1H), 3.60-

3.43 (m, 1H), 2.45-2.30 (m, 1H), 2.19-2.08 (m, 2H), 2.01-1.94 (m, 1H), 1.44 (s, 3H), 1.26 (s, 6H).

(S)-tert-Butyl-2-((3-(4-((4-(4-methoxyphenyl)-1H-1,2,3-triazol-1-yl)methyl)phenyl)-1,2,4-oxadiazol-5-yl)pyrrolidine-1-carboxylate (23d)

Synthesized by general procedure B: Yield: 81%; White solid; $^1$H NMR (400 MHz, CDCl$_3$) δ 8.07 (d, J=8.0 Hz, 2H), 7.71 (d, J=8.8 Hz, 2H), 7.60 (d, J=8.6 Hz, 1H), 7.38 (t, J=9.9 Hz, 2H), 6.92 (d, J=8.7 Hz, 2H), 5.60 (s, 2H), 5.21-5.00 (m, 1H), 3.81 (s, 3H), 3.73-3.45 (m, 2H), 2.44-2.30 (m, 1H), 2.19-2.06 (m, 2H), 2.01-1.94 (m, 1H), 1.44 (s, 3H), 1.26 (s, 6H).

(S)-tert-Butyl-2-((3-(4-((4-(thiophen-2-yl)-1H-1,2,3-triazol-1-yl)methyl)phenyl)-1,2,4-oxadiazol-5-yl)-pyrrolidine-1-carboxylate (23e)

Synthesized by general procedure B: Yield: 74%; Brown solid; $^1$H NMR (400 MHz, CDCl$_3$) δ 8.08 (d, J=7.7 Hz, 2H), 7.59 (d, J=7.8 Hz, 1H), 7.37 (dd, J=22.6, 5.6 Hz, 3H), 7.27 (d, J=5.2 Hz, 1H), 7.08-7.01 (m, 1H), 5.60 (s, 2H), 5.21-5.01 (m, 1H), 3.76-3.42 (m, 2H), 2.44-2.34 (m, 1H), 2.15-1.97 (m, 3H), 1.44 (s, 3H), 1.27 (s, 6H).

(S)-tert-Butyl-2-((3-(4-((4-butyl-1H-1,2,3-triazol-1-yl)methyl)phenyl)-1,2,4-oxadiazol-5-yl)-pyrrolidine-1-carboxylate (23f)

Synthesized by general procedure B: Yield: 85%; White solid; $^1$H NMR (400 MHz, CDCl$_3$) δ 8.05 (d, J=8.0 Hz, 2H), 7.32 (t, J=8.8 Hz, 2H), 7.19 (d, J=10.0 Hz, 1H), 5.53 (s, 2H), 5.21-5.03 (m, 1H), 3.72-3.60 (m, 1H), 3.57-3.44 (m, 1H), 2.68 (t, J=7.7 Hz, 2H), 2.42-2.31 (m, 1H), 2.18-2.08 (m, 2H), 2.01-1.95 (m, 1H), 1.65-1.58 (m, 2H), 1.44 (s, 3H), 1.34 (dd, J=14.9, 7.5 Hz, 2H), 1.27 (s, 6H), 0.89 (t, J=7.3 Hz, 3H).

(S)-tert-Butyl-2-((3-(4-((4-(4-(fluorophenyl)-1H-1,2,3-triazol-1-yl)methyl)phenyl)-1,2,4-oxadiazol-5-yl)pyrrolidine-1-carboxylate (23g)

Synthesized by general procedure B: Yield: 56%; White solid; $^1$H NMR (400 MHz, CDCl$_3$) δ 8.08 (d, J=7.7 Hz, 2H), 7.76 (dd, J=8.1, 5.5 Hz, 2H), 7.64 (d, J=9.4 Hz, 1H), 7.38 (t, J=10.1 Hz, 2H), 7.07 (t, J=8.6 Hz, 2H), 5.61 (s, 2H), 5.19-5.03 (m, 1H), 3.72-3.44 (m, 2H), 2.40-2.34 (m, 1H), 2.17-2.08 (m, 2H), 1.99-1.95 (m, 1H), 1.43 (s, 3H), 1.26 (s, 6H).

(S)-tert-Butyl-2-((3-(4-((4-cyclopropyl-1H-1,2,3-triazol-1-yl)methyl)phenyl)-1,2,4-oxadiazol-5-yl)pyrrolidine-1-carboxylate (23h)

Synthesized by general procedure B: Yield: 85%; White solid; $^1$H NMR (400 MHz, CDCl$_3$) δ 8.05 (d, J=7.9 Hz, 2H), 7.31 (t, J=10.5 Hz, 2H), 7.16 (t, J=7.5 Hz, 1H), 5.50 (s, 2H), 5.18-5.03 (m, 1H), 3.74-3.60 (m, 1H), 3.55-3.45 (m, 1H), 2.39-2.34 (m, 1H), 2.15-2.08 (m, 2H), 1.99-1.97 (m, 1H), 1.94-1.87 (m, 1H), 1.43 (s, 3H), 1.25 (s, 6H), 0.95-0.87 (m, 2H), 0.81 (d, J=3.9 Hz, 2H).

(S)-tert-Butyl-(((tert-butoxycarbonyl)imino)(2-((3-(4-((4-phenyl-1H-1,2,3-triazol-1-yl)methyl)phenyl)-1,2,4-oxadiazol-5-yl)pyrrolidin-1-yl)methyl)carbamate (24a)

Synthesized by general procedure C: Yield: 47%; White solid; $^1$H NMR (400 MHz, CDCl$_3$) δ 10.09 (s, 1H), 8.08 (d, J=8.3 Hz, 2H), 7.79 (d, J=7.1 Hz, 2H), 7.68 (s, 1H), 7.42-7.36 (m, 4H), 7.32-7.28 (m, 1H), 5.63 (s, 2H), 5.59 (dd, J=7.8, 4.5 Hz, 1H), 3.92-3.83 (m, 1H), 3.82-3.72 (m, 1H), 2.46-2.38 (m, 1H), 2.21-2.13 (m, 2H), 1.62 (s, 1H), 1.46 (s, 9H), 1.39 (s, 9H).

(S)-tert-Butyl-(((tert-butoxycarbonyl)imino)(2-((3-(4-((4-(4-(trifluoromethyl)phenyl)-1H-1,2,3-triazol-1-yl)methyl)phenyl)-1,2,4-oxadiazol-5-yl)pyrrolidin-1-yl)methyl)carbamate (24b)

Synthesized by general procedure C: Yield: 32%; White solid; $^1$H NMR (400 MHz, CDCl$_3$) δ 9.99 (s, 1H), 7.99 (d, J=8.1 Hz, 2H), 7.80 (d, J=8.1 Hz, 2H), 7.65 (s, 1H), 7.54 (d, J=8.2 Hz, 2H), 7.30 (d, J=8.1 Hz, 2H), 5.54 (s, 2H), 5.49 (dd, J=7.7, 4.4 Hz, 1H), 3.81-3.62 (m, 2H), 2.38-2.27 (m, 1H), 2.11-2.03 (m, 2H), 1.92-1.87 (m, 1H), 1.37-1.29 (m, 18H).

(S)-tert-Butyl-(((tert-butoxycarbonyl)imino)(2-((3-(4-((4-(pyridin-2-yl)-1H-1,2,3-triazol-1-yl)methyl)phenyl)-1,2,4-oxadiazol-5-yl)pyrrolidin-1-yl)methyl)carbamate (24c)

Synthesized by general procedure C: Yield: 25%; White solid; $^1$H NMR (400 MHz, CDCl$_3$) δ 10.11 (s, 1H), 8.52 (d, J=4.8 Hz, 1H), 8.16 (d, J=8.0 Hz, 1H), 8.07 (d, J=8.4 Hz, 3H), 7.75 (td, J=7.7, 1.4 Hz, 1H), 7.40 (d, J=8.1 Hz, 2H), 7.20 (dd, J=6.9, 5.5 Hz, 1H), 5.63 (s, 2H), 5.58 (dd, J=7.7, 4.5 Hz, 1H), 3.90-3.84 (m, 1H), 3.80-3.72 (m, 1H), 2.48-2.36 (m, 1H), 2.21-2.13 (m, 2H), 1.72 (br s, 1H), 1.46 (s, 9H), 1.39 (s, 9H).

(S)-tert-Butyl-(((tert-butoxycarbonyl)imino)(2-((3-(4-((4-(4-methoxyphenyl)-1H-1,2,3-triazol-1-yl)methyl)phenyl)-1,2,4-oxadiazol-5-yl)pyrrolidin-1-yl)methyl)carbamate (24d)

Synthesized by general procedure C: Yield: 33%; White solid; $^1$H NMR (400 MHz, CDCl$_3$) δ 10.08 (s, 1H), 8.07 (d, J=8.2 Hz, 2H), 7.71 (d, J=8.8 Hz, 2H), 7.59 (s, 1H), 7.37 (d, J=8.3 Hz, 2H), 6.91 (d, J=8.8 Hz, 2H), 5.60 (s, 2H), 5.59-5.56 (m, 1H), 3.91-3.83 (m, 1H), 3.81 (s, 3H), 3.79-3.72 (m, 1H), 2.48-2.38 (m, 1H), 2.20-2.13 (m, 2H), 1.66 (s, 1H), 1.46 (s, 9H), 1.39 (s, 9H).

(S)-tert-Butyl-(((tert-butoxycarbonyl)imino)(2-((3-(4-((4-(thiophen-2-yl)-1H-1,2,3-triazol-1-yl)methyl)phenyl)-1,2,4-oxadiazol-5-yl)pyrrolidin-1-yl)methyl)carbamate (24e)

Synthesized by general procedure C: Yield: 19%; Brown solid; $^1$H NMR (400 MHz, CDCl$_3$) δ 10.08 (s, 1H), 8.08 (d, J=8.2 Hz, 2H), 7.59 (s, 1H), 7.38 (d, J=8.2 Hz, 2H), 7.33 (d, J=4.6 Hz, 1H), 7.27 (d, J=5.1 Hz, 1H), 7.06-7.01 (m, 1H), 5.62-5.56 (m, 3H), 3.90-3.84 (m, 1H), 3.83-3.72 (m, 1H), 2.49-2.37 (m, 1H), 2.17-2.13 (m, 2H), 2.01-1.99 (m, 1H), 1.44 (br m, 18H).

(S)-tert-Butyl-(((tert-butoxycarbonyl)imino)(2-((3-(4-((4-butyl-1H-1,2,3-triazol-1-yl)methyl)phenyl)-1,2,4-oxadiazol-5-yl)pyrrolidin-1-yl)methyl)carbamate (24f)

Synthesized by general procedure C: Yield: 19%; White solid; $^1$H NMR (400 MHz, CDCl$_3$) δ 10.09 (s, 1H), 8.05 (d, J=8.2 Hz, 2H), 7.32 (d, J=8.1 Hz, 2H), 7.24 (s, 1H), 5.58 (dd, J=7.6, 4.5 Hz, 1H), 5.53 (s, 2H), 3.90-3.84 (m, 1H), 3.82-

3.74 (m, 1H), 2.69 (t, J=7.7 Hz, 2H), 2.48-2.38 (m, 1H), 2.21-2.17 (m, 2H), 2.02-1.97 (m, 1H), 1.65-1.57 (m, 2H), 1.46 (s, 9H), 1.40 (s, 9H), 1.24 (t, J=6.6 Hz, 2H), 0.89 (t, J=7.3 Hz, 3H).

(S)-tert-Butyl-(((tert-butoxycarbonyl)imino)(2-((3-(4-((4-(4-fluorophenyl)-1H-1,2,3-triazol-1-yl)methyl)phenyl)-1,2,4-oxadiazol-5-yl)pyrrolidin-1-yl)methyl)carbamate (24g)

Synthesized by general procedure C: Yield: 35%; White solid; $^1$H NMR (400 MHz, CDCl$_3$) δ 10.09 (s, 1H), 8.08 (d, J=8.2 Hz, 2H), 7.76 (dd, J=8.2, 5.9 Hz, 2H), 7.63 (s, 1H), 7.38 (d, J=8.0 Hz, 2H), 7.07 (t, J=8.7 Hz, 2H), 5.62 (s, 2H), 5.59 (dd, J=7.8, 4.4 Hz, 1H), 3.90-3.75 (m, 2H), 2.46-2.40 (m, 1H), 2.22-2.13 (m, 2H), 2.02-1.97 (m, 1H), 1.46 (s, 9H), 1.39 (s, 9H).

(S)-tert-Butyl-(((tert-butoxycarbonyl)imino)(2-((3-(4-((4-cyclopropyl-1H-1,2,3-triazol-1-yl)methyl)phenyl)-1,2,4-oxadiazol-5-yl)pyrrolidin-1-yl)methyl)carbamate (24h)

Synthesized by general procedure C: Yield: 16%; White solid; $^1$H NMR (400 MHz, CDCl$_3$) δ 10.08 (s, 1H), 8.04 (d, J=8.1 Hz, 2H), 7.31 (d, J=8.0 Hz, 2H), 7.14 (s, 1H), 5.58 (dd, J=7.6, 4.4 Hz, 1H), 5.50 (s, 2H), 3.92-3.72 (m, 2H), 2.50-2.38 (m, 1H), 2.19-2.13 (m, 2H), 2.00-1.87 (m, 1H), 1.72 (br s, 1H), 1.46 (s, 9H), 1.39 (s, 9H), 0.93-0.88 (m, 2H), 0.83-0.79 (m, 2H).

(S)-2-((3-(4-((4-Phenyl-1H-1,2,3-triazol-1-yl)methyl)phenyl)-1,2,4-oxadiazol-5-yl)pyrrolidine-1-carboximidamide hydrochloride (25a)

Synthesized by general procedure D: Yield: 81%; White solid; $^1$H NMR (400 MHz, CD$_3$OD) δ 8.57 (s, 1H), 8.12 (dd, J=19.3, 8.1 Hz, 2H), 7.82 (d, J=7.7 Hz, 2H), 7.57 (t, J=7.8 Hz, 2H), 7.46 (t, J=7.6 Hz, 2H), 7.38 (t, J=7.3 Hz, 1H), 5.80 (d, J=4.2 Hz, 2H), 5.48-5.18 (m, 1H), 3.78-3.53 (m, 2H), 2.72-2.52 (m, 1H), 2.47-2.37 (m, 1H), 2.32-2.20 (m, 1H), 2.15-2.02 (m, 1H); $^{13}$C NMR (101 MHz, DMSO-d$_6$) δ 178.77, 175.79, 167.72, 167.70, 155.90, 147.11, 140.24, 140.03*, 131.01, 129.33, 129.21, 128.37, 128.01, 126.00*, 125.76*, 125.60, 122.33, 122.28*, 55.18, 53.19, 53.01*, 48.10*, 45.75, 31.81, 29.09, 23.72, 23.27*; HRMS (ESI) m/z [M×H]$^+$ calcd. for C$_{22}$H$_{23}$N$_8$O 415.1989, found 415.1987.

(S)-2-((3-(4-((4-(4-(Trifluoromethyl)phenyl)-1H-1,2,3-triazol-1-yl)methyl)phenyl)-1,2,4-oxadiazol-5-yl)pyrrolidine-1-carboximidamide hydrochloride (25b)

Synthesized by general procedure D: Yield: 78%; White solid; $^1$H NMR (400 MHz, CD$_3$OD) δ 8.54 (d, J=10.7 Hz, 1H), 8.09 (d, J=8.1 Hz, 1H), 8.02 (d, J=8.1 Hz, 2H), 7.97 (d, J=8.2 Hz, 1H), 7.73 (d, J=8.2 Hz, 2H), 7.54 (d, J=8.1 Hz, 1H), 7.48 (d, J=8.2 Hz, 1H), 5.75 (d, J=10.5 Hz, 2H), 5.44 (d, J=7.7 Hz, 1H), 3.76 (td, J=9.2, 2.3 Hz, 1H), 3.61 (dt, J=17.2, 8.7 Hz, 1H), 2.61-2.41 (m, 2H), 2.29-2.17 (m, 1H), 2.16-2.01 (m, 1H); $^{13}$C NMR (101 MHz, DMSO-d$_6$) δ 178.76, 171.95, 167.76*, 167.69, 155.81, 145.73, 139.82, 138.92*, 134.99, 129.30, 128.90, 128.03, 127.71, 127.60, 126.34, 126.31, 126.14, 126.08*, 123.55, 123.48*, 55.20, 53.23*, 53.15, 48.10, 31.82, 23.28; HRMS (ESI) m/z [M×H]$^+$ calcd. for C$_{23}$H$_{22}$F$_3$N$_8$O 483.1863, found 483.1857.

(S)-2-(3-(4-((4-(Pyridin-2-yl)-1H-1,2,3-triazol-1-yl)methyl)phenyl)-1,2,4-oxadiazol-5-yl)pyrrolidine-1-carboximidamide hydrochloride (25c)

Synthesized by general procedure D: Yield: 71%; White solid; $^1$H NMR (400 MHz, CD$_3$OD) δ 9.04 (s, 1H), 8.77 (d, J=5.7 Hz, 1H), 8.62 (t, J=8.1 Hz, 1H), 8.45 (d, J=8.1 Hz, 1H), 8.17-8.08 (m, 2H), 7.96 (t, J=6.7 Hz, 1H), 7.60 (d, J=8.2 Hz, 2H), 5.87 (s, 2H), 5.45 (dd, J=8.0, 1.1 Hz, 1H), 3.76 (td, J=9.2, 2.0 Hz, 1H), 3.65-3.58 (m, 1H), 2.61-2.42 (m, 2H), 2.31-2.20 (m, 1H), 2.13-2.01 (m, 1H); $^{13}$C NMR (101 MHz, DMSO-d$_6$) δ 178.79, 175.74*, 167.64, 155.92, 145.47*, 144.98, 143.88, 142.57*, 139.41, 129.44, 128.04, 126.48, 126.18, 125.31, 122.63, 55.20, 53.36, 53.17*, 48.13, 45.73*, 31.80, 29.09*, 23.74*, 23.27; HRMS (ESI) m/z [M×H]$^+$ calcd. for C$_{21}$H$_{22}$N$_9$O 416.1942, found 416.1941.

(S)-2-((3-(4-((4-(4-Methoxyphenyl)-1H-1,2,3-triazol-1-yl)methyl)phenyl)-1,2,4-oxadiazol-5-yl)-pyrrolidine-1-carboximidamide hydrochloride (25d)

Synthesized by general procedure D: Yield: 89%; White solid; $^1$H NMR (400 MHz, CD$_3$OD) δ 8.61 (s, 1H), 8.11 (dd, J=18.9, 8.2 Hz, 2H), 7.75 (d, J=8.7 Hz, 2H), 7.59 (d, J=8.1 Hz, 2H), 7.04 (d, J=8.7 Hz, 2H), 5.83 (s, 2H), 5.45 (d, J=7.0 Hz, 1H), 3.84 (s, 3H), 3.79-3.74 (m, 1H), 3.65-3.58 (m, 1H), 2.62-2.42 (m, 1H), 2.28-2.03 (m, 2H); $^{13}$C NMR (101 MHz, DMSO-d$_6$) δ 178.76, 175.78*, 167.70, 159.46, 155.89, 147.04, 140.09, 129.18, 127.99, 126.97, 125.98*, 123.59, 121.30, 114.73, 55.59, 55.18, 53.20*, 52.98, 48.10, 45.76*, 31.81, 29.09*, 23.72*, 23.27; HRMS (ESI) m/z [M×H]$^+$ calcd. for C$_{23}$H$_{25}$N$_8$O$_2$ 445.2095, found 445.2092.

(S)-2-((3-(4-((4-(Thiophen-2-yl)-1H-1,2,3-triazol-1-yl)methyl)phenyl)-1,2,4-oxadiazol-5-yl)-pyrrolidine-1-carboximidamide hydrochloride (25e)

Synthesized by general procedure D: Yield: 51%; Brown solid; $^1$H NMR (400 MHz, CD$_3$OD) δ 8.35-8.29 (m, 2H), 8.09 (d, J=8.1 Hz, 1H), 7.56-7.49 (m, 2H), 7.42 (d, J=4.2 Hz, 2H), 7.11-7.07 (m, 1H), 5.72 (s, 2H), 5.45 (d, J=7.9 Hz, 1H), 3.80-3.72 (m, 1H), 3.66-3.57 (m, 1H), 2.61-2.41 (m, 2H), 2.31-2.18 (m, 1H), 2.15-2.03 (m, 1H); $^{13}$C NMR (101 MHz, DMSO-d$_6$) δ 178.76, 167.70, 155.83, 142.50, 139.89, 133.68*, 133.25, 129.24, 128.33, 128.02, 126.04*, 125.89, 124.67, 121.52, 105.29, 55.19, 53.04, 48.10, 31.82, 31.73*, 23.70*, 23.28; HRMS (ESI) m/z [M×H]$^+$ calcd. for C$_{20}$H$_{21}$N$_8$OS 421.1554, found 421.1550.

(S)-2-((3-(4-((4-Butyl-1H-1,2,3-triazol-1-yl)methyl)phenyl)-1,2,4-oxadiazol-5-yl)pyrrolidine-1-carboximidamide hydrochloride (25f)

Synthesized by general procedure D: Yield: 73%; White solid; $^1$H NMR (400 MHz, CD$_3$OD) δ 8.34 (d, J=2.1 Hz, 1H), 8.11 (d, J=8.0 Hz, 2H), 7.58 (d, J=7.8 Hz, 2H), 5.83 (s, 2H), 5.46 (d, J=7.8 Hz, 1H), 3.77 (t, J=8.2 Hz, 1H), 3.64-3.58 (m, 1H), 2.82 (t, J=7.7 Hz, 2H), 2.60-2.45 (m, 2H), 2.29-2.03 (m, 2H), 1.75-1.65 (m, 2H), 1.46-1.35 (m, 2H), 0.96 (t, J=7.3 Hz, 3H); $^{13}$C NMR (101 MHz, DMSO-d$_6$) δ 178.74, 167.70, 155.85, 147.61, 140.31, 129.10, 127.93, 125.88, 122.74, 55.18, 52.71, 48.09, 31.81*, 31.46, 25.02, 23.27*, 22.08, 14.11; HRMS (ESI) m/z [M×H]$^+$ calcd. for $C_{20}H_{27}N_8O$ 395.2302, found 395.2297.

(S)-2-((3-(4-((4-(4-Fluorophenyl)-1H-1,2,3-triazol-1-yl)methyl)phenyl)-1,2,4-oxadiazol-5-yl)-pyrrolidine-1-carboximidamide hydrochloride (25g)

Synthesized by general procedure D: Yield: 79%; White solid; $^1$H NMR (400 MHz, CD$_3$OD) δ 8.49 (s, 1H), 8.34 (d, J=2.6 Hz, 1H), 8.15-8.07 (m, 2H), 7.85 (dd, J=8.3, 5.5 Hz, 2H), 7.55 (d, J=8.1 Hz, 2H), 7.19 (t, J=8.7 Hz, 2H), 5.77 (s, 2H), 5.45 (d, J=7.6 Hz, 1H), 3.76 (td, J=9.1, 2.0 Hz, 1H), 3.63-3.57 (m, 1H), 2.61-2.41 (m, 2H), 2.30-2.19 (m, 1H), 2.13-2.01 (m, 1H); $^{13}$C NMR (101 MHz, DMSO-d$_6$) δ 178.34, 167.28, 160.58*, 155.43, 145.83, 139.56, 133.33, 128.79, 127.59, 127.26*, 127.18, 125.59, 121.75, 115.95, 115.74*, 105.29, 54.77, 52.62, 47.67, 45.38*, 31.40, 22.86; HRMS (ESI) m/z [M×H]$^+$ calcd. for $C_{22}H_{22}FN_8O$ 433.1895, found 433.1888.

(S)-2-((3-(4-((4-Cyclopropyl-1H-1,2,3-triazol-1-yl)methyl)phenyl)-1,2,4-oxadiazol-5-yl)pyrrolidine-1-carboximidamide hydrochloride (25h)

Synthesized by general procedure D: Yield: 71%; White solid; $^1$H NMR (400 MHz, CD$_3$OD) δ 8.28 (s, 1H), 8.13 (dd, J=18.9, 8.2 Hz, 2H), 7.61-7.54 (m, 2H), 5.79 (s, 2H), 5.46 (d, J=8.0 Hz, 1H), 3.82-3.73 (m, 1H), 3.63-3.56 (m, 1H), 2.62-2.43 (m, 2H), 2.30-2.21 (m, 1H), 2.13-2.06 (m, 2H), 1.19-1.12 (m, 2H), 0.95-0.88 (m, 2H); $^{13}$C NMR (101 MHz, DMSO-d$_6$) δ 178.75, 175.76*, 167.69, 155.90, 149.64, 140.35*, 140.16, 133.12, 129.13, 129.02*, 127.93, 125.91, 125.67, 121.75*, 121.70, 55.18, 53.18*, 52.80, 48.09, 45.74*, 31.80, 31.72*, 23.72*, 23.27, 8.14, 6.89; HRMS (ESI) m/z [M×H]$^+$ calcd. for $C_{19}H_{23}N_8O$ 379.1989, found 379.1996.

4-(Azidomethyl)-N'-((1-cyanocyclopropanecarbonyl)oxy) benzimidamide (26)

To a suspension of 1-cyanopropanecarboxylic acid (0.29 g, 2.61 mmol), PyBOP (1.36 g, 2.61 mmol), and 17 (0.5 g, 2.61 mmol) in CH$_2$Cl$_2$ (10 mL) at rt was added DIEA (1.8 mL, 10.44 mmol) and was stirred for 4 h until the reaction was completed as determined by the TLC. The reaction was then evaporated to dryness and immediately purified by silica gel column chromatography, to afford 26 (0.4 g, 54% yield) as a white solid. $^1$H NMR (400 MHz, CDCl$_3$) δ 7.71 (d, J=8.1 Hz, 2H), 7.37 (d, J=8.0 Hz, 2H), 5.28 (s, 2H), 4.38 (s, 2H), 1.81 (dd, J=8.4, 4.6 Hz, 2H), 1.69 (dd, J=8.4, 4.6 Hz, 2H).

1-(3-(4-(Azidomethyl)phenyl)-1,2,4-oxadiazol-5-yl)cyclopropanecarbonitrile (27)

To a solution of compound 26 (0.4 g, 1.40 mmol) in THF (2 mL) at rt was added a 1.0 M solution of TBAF in THF (0.4 mL, 1.40 mmol) and was stirred for 2 h until the reaction was completed as determined by the TLC. The reaction was evaporated to dryness and immediately purified by silica gel column chromatography, to afford 27 (0.25 g, 68% yield) as a white solid. $^1$H NMR (400 MHz, CDCl$_3$) δ 8.05 (d, J=8.0 Hz, 2H), 7.42 (d, J=8.1 Hz, 2H), 4.41 (s, 2H), 2.02 (s, 4H).

1-(3-(4-((4-Phenyl-1H-1,2,3-triazol-1-yl)methyl)phenyl)-1,2,4-oxadiazol-5-yl)cyclopropanecarbonitrile (28a)

Synthesized by general procedure B: Yield: 62%; White solid; $^1$H NMR (400 MHz, DMSO-d$_6$) δ 8.69 (s, 1H), 8.00 (d, J=8.2 Hz, 2H), 7.86 (d, J=7.8 Hz, 2H), 7.52 (d, J=8.2 Hz, 2H), 7.45 (t, J=7.6 Hz, 2H), 7.33 (t, J=7.4 Hz, 1H), 5.76 (s, 2H), 2.20 (dd, J=8.8, 5.0 Hz, 2H), 2.02 (dd, J=8.8, 5.0 Hz, 2H).

1-(3-(4-((4-(1-Methyl-1H-pyrazol-5-yl)-1H-1,2,3-triazol-1-yl)methyl)phenyl)-1,2,4-oxadiazol-5-yl)cyclo-propanecarbonitrile (28b)

Synthesized by general procedure B: Yield: 72%; White solid; $^1$H NMR (400 MHz, CDCl$_3$) δ 8.03 (d, J=8.3 Hz, 2H), 7.76 (s, 1H), 7.68 (s, 1H), 7.49 (s, 1H), 7.36 (d, J=8.2 Hz, 2H), 5.58 (s, 2H), 3.91 (s, 3H), 2.01 (s, 4H).

1-(3-(4-((4-Cyclopropyl-1H-1,2,3-triazol-1-yl)methyl)phenyl)-1,2,4-oxadiazol-5-yl)cyclopropanecarbonitrile (28c)

Synthesized by general procedure B: Yield: 85%; White solid; $^1$H NMR (400 MHz, CDCl$_3$) δ 8.01 (d, J=8.1 Hz, 2H), 7.31 (d, J=8.1 Hz, 2H), 7.17 (s, 1H), 5.50 (s, 2H), 2.05-1.96 (m, 4H), 1.95-1.86 (m, 1H), 0.95-0.87 (m, 2H), 0.86-0.77 (m, 2H).

1-(3-(4-((4-Phenyl-1H-1,2,3-triazol-1-yl)methyl)phenyl)-1,2,4-oxadiazol-5-yl)cyclopropanecarboximidamide hydrochloride (29a)

Synthesized by general procedure E: Yield: 51%; White solid; $^1$H NMR (400 MHz, CD$_3$OD) δ 8.43 (s, 1H), 8.08 (d, J=8.1 Hz, 2H), 7.82 (d, J=7.7 Hz, 2H), 7.53 (d, J=7.9 Hz, 2H), 7.43 (t, J=7.3 Hz, 2H), 7.34 (t, J=7.4 Hz, 1H), 5.75 (s, 2H), 2.02-1.91 (m, 4H); $^{13}$C NMR (101 MHz, DMSO-d$_6$) δ 177.93, 167.80, 166.15, 147.04, 140.12, 130.98, 129.33, 129.19, 128.37, 127.97, 125.81*, 125.57, 122.37, 52.97, 22.50, 18.88; HRMS (ESI) m/z [M×H]$^+$ calcd. for $C_{21}H_{20}N_7O$ 386.1724, found 386.1722.

1-(3-(4-((4-(1-Methyl-1H-pyrazol-5-yl)-1H-1,2,3-triazol-1-yl)methyl)phenyl)-1,2,4-oxadiazol-5-yl)cyclopropanecarboximidamide hydrochloride (29b)

Synthesized by general procedure E: Yield: 59%; White solid; $^1$H NMR (400 MHz, CD$_3$OD) δ 8.15 (d, J=4.8 Hz, 1H), 8.05 (t, J=8.2 Hz, 2H), 7.94 (d, J=2.6 Hz, 1H), 7.79 (s, 1H), 7.49 (dd, J=7.9, 6.0 Hz, 2H), 5.69 (d, J=2.9 Hz, 2H), 3.91 (s, 3H), 2.11-1.93 (m, 4H); $^{13}$C NMR (101 MHz, DMSO-d$_6$) δ 177.96, 167.85, 166.01, 140.80, 140.25, 136.63, 129.17, 129.13*, 128.40, 128.00*, 127.97, 125.78, 125.69*, 120.84, 112.96, 52.82, 39.02, 22.60, 21.11, 18.73; HRMS (ESI) m/z [M×H]$^+$ calcd. for $C_{19}H_{20}N_9O$ 390.1785, found 390.1778.

1-(3-(4-((4-Cyclopropyl-1H-1,2,3-triazol-1-yl)methyl)phenyl)-1,2,4-oxadiazol-5-yl)cyclopropanecarboximidamide hydrochloride (29c)

Synthesized by general procedure E: Yield: 55%; White solid; $^1$H NMR (400 MHz, DMSO-d$_6$+CDCl$_3$) δ 8.05-7.80 (m, 5H), 5.60 (d, J=16.3 Hz, 2H), 2.04-1.81 (m, 4H), 1.16 (t, J=7.1 Hz, 1H), 0.88 (d, J=6.0 Hz, 2H), 0.72-0.63 (br m, 2H);

¹³C NMR (101 MHz, DMSO-d₆) δ 177.93, 167.83, 166.14, 149.70, 140.36, 129.09, 127.91, 121.62, 52.67, 22.52, 21.21*, 18.83, 14.52, 8.10, 6.95; HRMS (ESI) m/z [M×H]⁺ calcd. for $C_{18}H_{20}N_7O$ 350.1724, found 350.1723.

Biological Evaluations

Protein Sequence Alignment Analysis

Protein sequence alignment analysis was performed using Clustal Omega multiple sequence alignment tool (F. Sievers, et al., Mol. Syst. Biol. 7 (2011) 539). Proteins sequences of human SphK1 protein (UniProtKB: Q9NYA1) and hu-man SphK2 protein (UniProtKB: Q9NRA0) were used and compared.

In Vitro Sphingosine Kinase Assay

ADP-Glo (Promega, Madison, WI) kinase assay were used to evaluate the kinase activity of SphK. ATP to ADP standard curves were prepared in the kinase buffer to assess the linearity of the assay in order to calculate the amount of ADP produced in each tested conditions (FIG. 4A). SB10 (tenfold signal to background ra-tio) of SphK was also determined to evaluate the enzyme perfor-mance and to optimize the kinase reaction condition in this system. In brief, for SphK2, 100 μM of ATP, 100 μM of D-erythro-Sphingosine (Tocris Bioscience, Minneapolis, MN), and 2 ng of recombinant human SphK2 (R&D Systems, Minneapolis, MN) with desired concentration of each synthesized compound were used for SphK2 kinase reaction. For SphK1, exact same reaction condition was used except 0.5 ng of recombinant human SphK1 was used.

To evaluate the SphK selectivity of each compound, 125 μM of each compound in reaction buffer (40 μM Tris, pH 8.0, 20 μM $MgCl_2$, and 0.1 mg/mL BSA) with 5% DMSO was incubated with either SphK1 or SphK2 in a 384-well solid white low volume microplate (Corning, Corning, NY), and the reaction was initiated by adding mixture of ATP and D-erythro-Sphingosine to a total volume of 5 μL, after 1 h incubation at room temperature with gentle shaking, the reaction was stopped by adding equal volume of ADP-Glo buffer and incubated for another hour to remove excess amount of ATP from the reaction. Afterwards, 10 μL of kinase detection reagent was added, mixed, and incubated for 30 min under dark. Luminescence output was recorded using a SpectraMax M5 Multi-Mode Microplate Readers (Molecular Devices, San Jose, CA), an integration time of 500 ms was used. All reactions were performed in triplicate. The enzyme activity of SphK in the presence of each compound was normalized to the no treatment control. To determine the $IC_{50}$ of each compound on SphK2, series dilutions of each compound ranging from 1.25 mM to 1.25 μM were tested in the presence of 50 μM of ATP. The final data was calculated using Prism 7.0 (GraphPad Software, La Jolla, CA), $IC_{50}$ was determined using Nonlinear regression (curve fit) four parameters dose-response calculations.

Molecular Modeling and Molecular Docking

The homology model for SphK2 was developed using the I-TASSER server with the canonical sequence of SphK2 (UniProtKB: Q9NRAO-1). A total of 5 models were produced, and the second ranking model was selected (C-score=2.36) following visual inspection and comparison with known structures of SphK1. The homology model was further refined using the protein preparation wizard in Maestro through side chain protonation (pH 5-9), h-bond optimization and a restrained minimization (heavy atoms converged to 0.3 Å) (Schrödinger Release 2018-4: Maestro, version 11.8, Schro€dinger, LLC, New York, NY (2018) Schrödinger Suite 2018 Protein Preparation Wizard, Schrödinger, LLC, New York (2018). Three-dimensional representations and protonation state of compound 29a were prepared using Ligprep (LigPrep, Schrodinger, LLC, New York (2015)). The induced fit docking protocol was carried out with extended sampling, and the binding site was identified by aligning the SphK2 homology model with SphK1 (PDB: 4V24) (W. Sherman, et al., J. Med. Chem. 49 (2006) 534e553). The resulting ensemble of docking poses were clustered by protein interaction fingerprint and the top scoring poses from each cluster were selected for binding pose metadynamics (Z. Deng, et al., J. Med. Chem. 47 (2004) 337e344). Binding pose metadynamics (ten simulations of 10 ns) were carried out on an NVIDIA P100 GPU using default parameters as previously described (A. J. Clark, et al., J. Chem. Theor. Comput. 12 (2016) 2990e2998). The top-scoring pose (Pose Score=1.2) was selected for further analysis.

In Vitro Cell Viability Assays

Figure 7A:
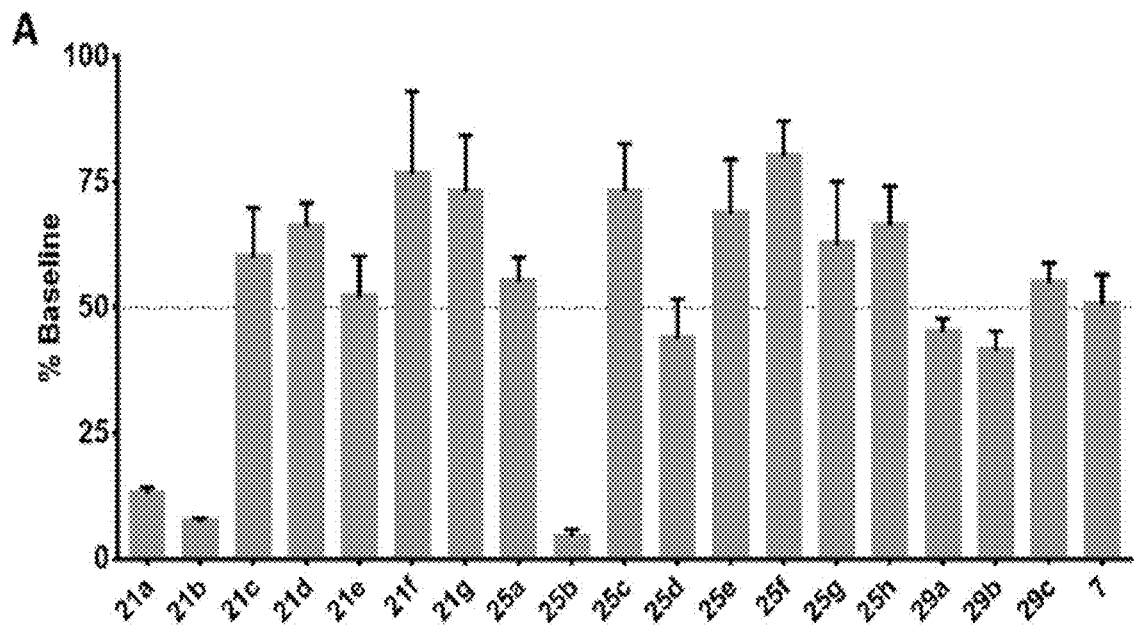
FIG. 7A depicts the antitumor activity of the compounds on U-251 MG glioblastoma tumor cells. The antitumor activities of all compounds on U-251 MG cell viability were measured and presented as % baseline with no inhibitor added. Each compound at concentration of 125 μM was tested in triplicate. Error bar indicates S. E. All tested compounds are able to reduce glioblastoma cell viability; three compounds 21a, 21b, and 25b caused the significant reduction of glioblastoma cell viability, suggesting the three compounds had the strongest antitumor activity.
Figure 7B:
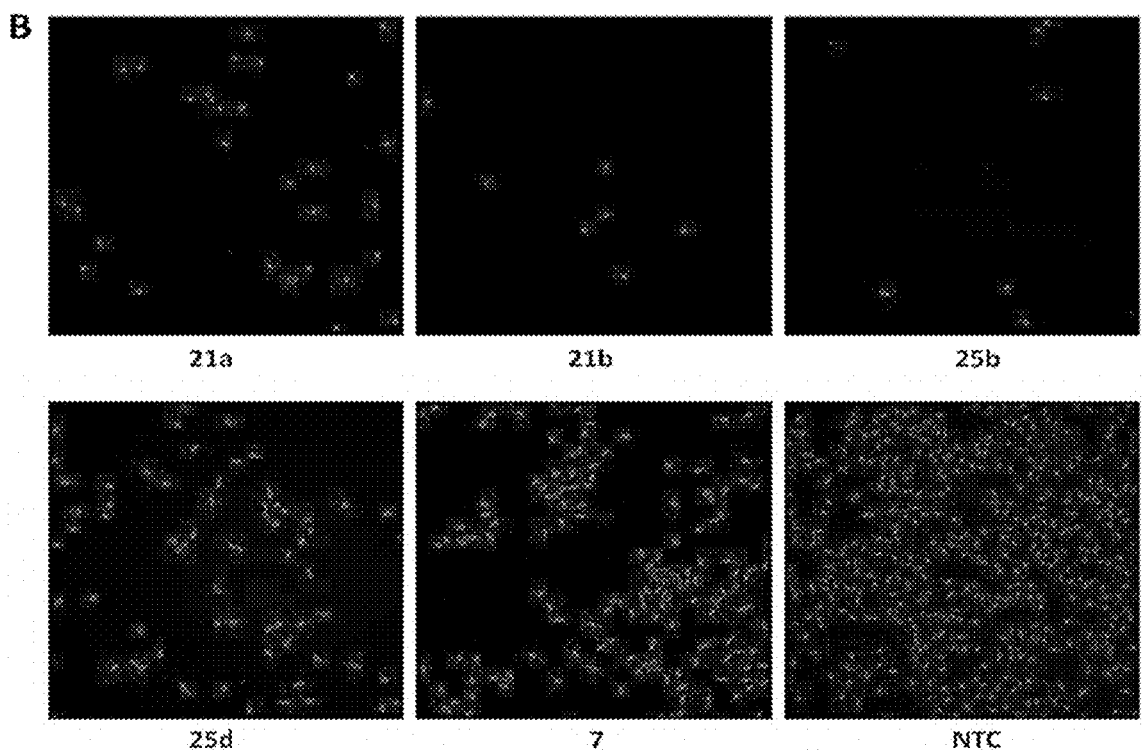
FIG. 7B depicts representative images of Hoechst 33258 stained cells after the treatments from selected compounds as analyzed in FIG. 7A. NTC is no treatment control.

For the assays of FIG. 7A-7B, U-251 MG cells were cultured in RPMI-1640 suppled with 10% FBS, 1 mM Sodium Pyruvate, and 1× Pen-Strep (ThermoFisher, Waltham, MA) and maintained at 37° C. and 5% $CO_2$ incubator. Cells were seeded into a 96-well microplate (Corning, Corning, NY) at 3000 cells/well and incubated for approximately 16 h. After that, medium was replaced with fresh medium con-taining 125 μM of each compound and incubated for 24 h. Cell viability was determined by staining with Hoechst 33258 for total cells and propidium iodide for apoptotic cells (Biotium, Fremont, CA). Cells were imaged using MetaXpress High-Content Image Acquisition and Analysis Software 6.1 and ImageXpress Micro XLS Widefield High-Content Analysis System (Molecular Devices, San Jose, CA). Images were taken with a Nikon 10 CFI Plan Fluor objective. For all samples, triplicated measurements were performed. All images were processed and analyzed automatically using batch processing in Fiji ImageJ (J. Schindelin, et al., Nat. Methods 9 (2012) 676e682).

For the assays of FIGS. 8 and 9, U-251 MG cells, SiHa cells, BT20 cells, or MDA-MB-452 cells were treated with increasing dose ($10^{-10}$ M to $10^{-4}$M) of SphK2 inhibitors (TZ72-45 (21a), TZ72-53 (21b), TZ72-109 (25b), or TZ72-141 (25d)) in biological replicates of five for 72h. Cell viability was determined using CellTiter96 MTS Assay and compared to DMSO treated control cells. $IC_{50}$ values were calculated by non-linear regression analysis of the dose-response curve using GraphPad Prism version 8.00 for Windows (GraphPad Software).

What is claimed is:

1. An SphK2 inhibiting agent formula 21, 25, or 29:

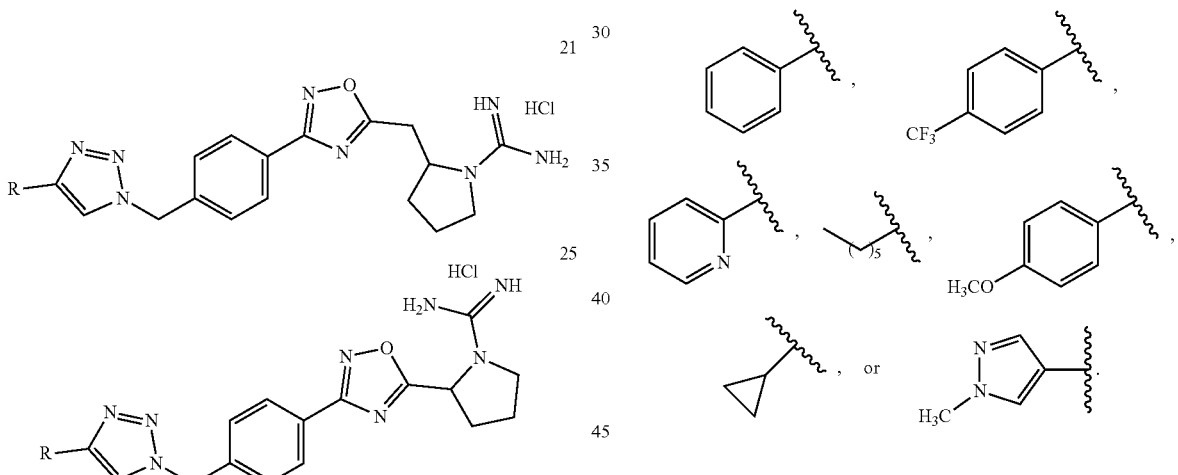

wherein R is substituted or unsubstituted aryl, substituted or unsubstituted alkyl, substituted or unsubstituted cycloalkyl, substituted or unsubstituted heterocyclo, or substituted or unsubstituted heteroaryl, or pharmaceutically acceptable salt.

2. The SphK2 inhibiting agent of claim 1, wherein R is phenyl, trifluoromethyl phenyl, pyridyl, $C_3$-$C_8$ alkyl, methoxyphenyl, cyclopropyl, thienyl, or fluorophenyl.

3. The SphK2 inhibiting agent of claim 1, wherein R is

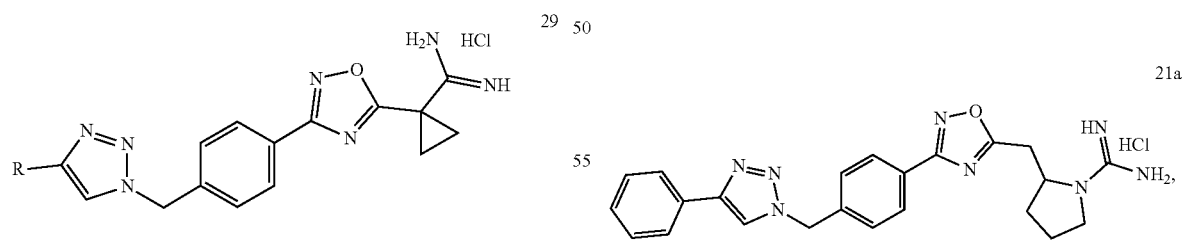

4. The SphK2 inhibiting agent of claim 1, wherein the SphK2 inhibiting agent is selected from:

21a

21b

-continued

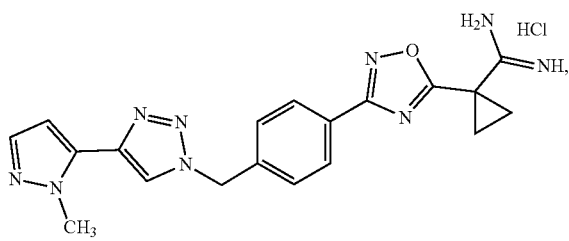

29b

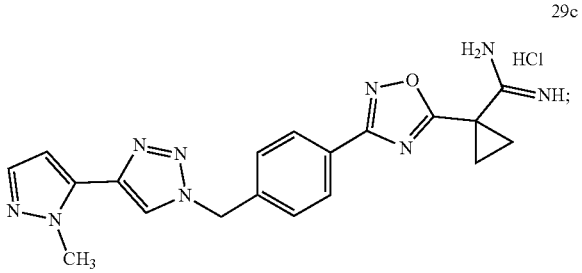

29c or a pharmaceutically acceptable salt.

5. The SphK2 inhibiting agent of claim 4 having the structure selected from:

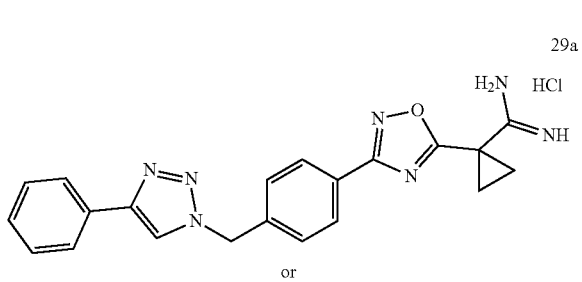

29a or

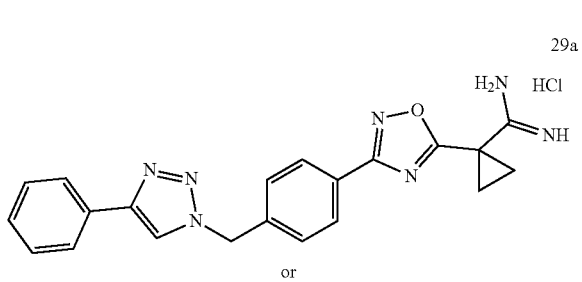

29b

6. The SphK2 inhibiting agent of claim 4 having the structure selected from:

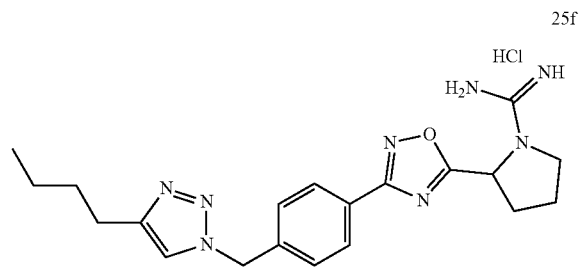

25f

-continued or

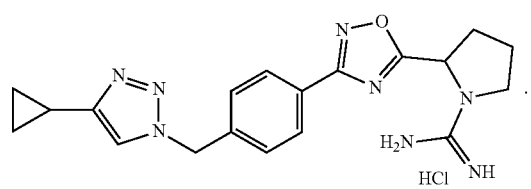

25h

7. The SphK2 inhibiting agent of claim 4, having the structure selected from:

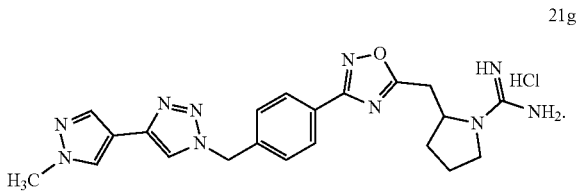 [SMILES: Cn1cc(-c2cn(Cc3ccc(-c4noc(CC5CCCN5C(=N)N)n4)cc3)nn2)cn1 ; Cl]

21g

8. The SphK2 inhibiting agent of claim 4 having the structure selected from:

21a

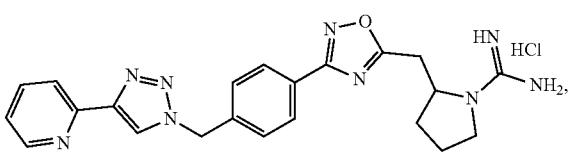

21c or

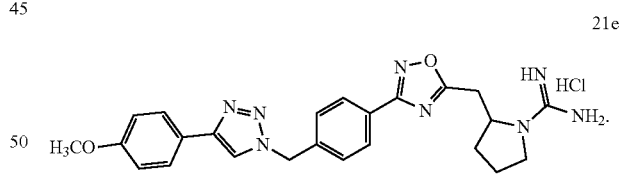

21e

9. The SphK2 inhibiting agent of claim 4 having the structure selected from:

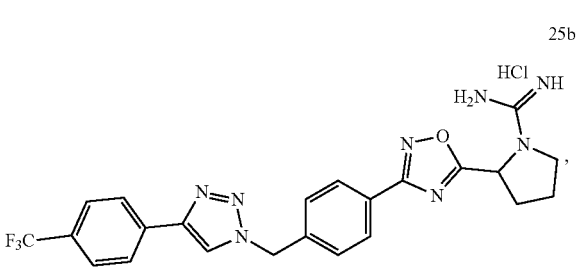

25b

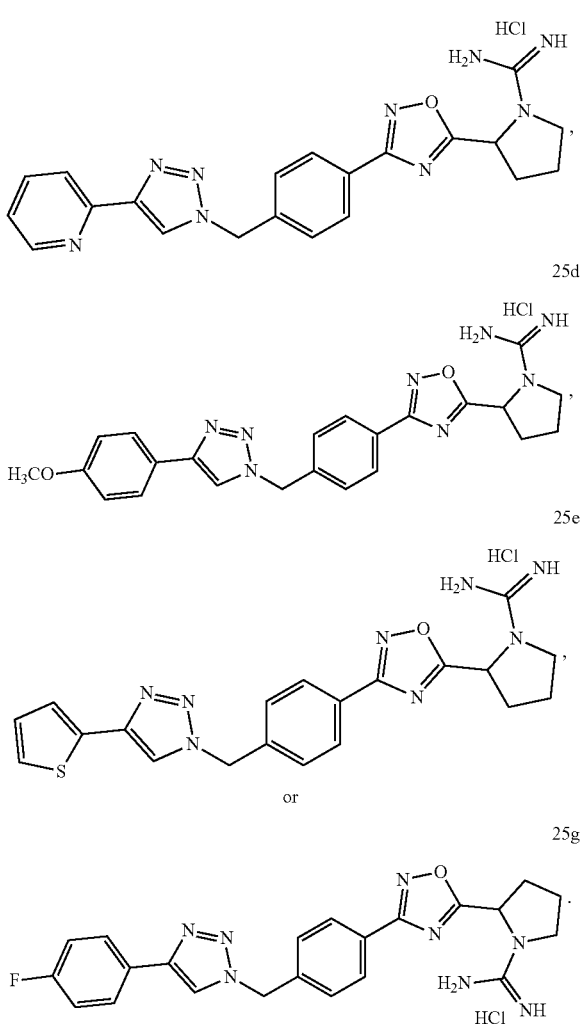

10. A pharmaceutical composition comprising a pharmaceutically acceptable excipient and the SphK2 inhibiting agent of claim 1.

11. The pharmaceutical composition of claim 10, wherein the pharmaceutically acceptable excipient is a solvent, a dispersion media, a coating, an antibacterial and antifungal agent, an isotonic agent, an absorption delaying agent, or a combination thereof.

12. A method of making an SphK2 inhibiting agent of claim 1 comprising:
  (1) coupling of amide-oxime derivatives with (S)-2-(1-(tert-butoxycarbonyl)pyrrolidin-2-yl)acetic acid/N-(tert-butoxycarbonyl)-L-proline to make the 1,2,4-oxadiazole motif with polar head groups;
  (2) employing copper catalyzed version of a Huisgen azide-alkyne cycloaddition protocol to make different 1,2,3-triazole derivatives on the terminal region; and/or
  (3) deprotecting t-Boc protecting groups with TFA and guanylation of amines followed by deprotection of di t-Boc protecting groups with HCl.

13. A method of inhibiting SphK2 in a subject comprising administering an SphK2 inhibiting agent of claim 1 to the subject, wherein the subject has an SphK2-associated disease, disorder, or condition.

14. A method of treating an SphK2-associated disease, disorder, or condition comprising administering a therapeutically effective amount of an SphK2 inhibiting agent of claim 1, to a subject in need thereof, wherein the subject has an SphK2-associated disease, disorder, or condition.

15. The method of claim 14, wherein the subject is a mammal.

16. The method of claim 15, wherein the subject is a human.

17. The method of claim 14, wherein the SphK2-associated disease is a glioblastoma.

* * * * *

SEQUENCE LISTING

```
Sequence total quantity: 2
SEQ ID NO: 1            moltype = AA   length = 384
FEATURE                 Location/Qualifiers
source                  1..384
                        mol_type = protein
                        organism = Homo sapiens
```

```
SEQUENCE: 1
MDPAGGPRGV LPRPCRVLVL LNPRGGKGKA LQLFRSHVQP LLAEAEISFT LMLTERRNHA    60
RELVRSEELG RWDALVVMSG DGLMHEVVNG LMERPDWETA IQKPLCSLPA GSGNALAASL   120
NHYAGYEQVT NEDLLTNCTL LLCRRLLSPM NLLSLHTASG LRLFSVLSLA WGFIADVDLE   180
SEKYRRLGEM RFTLGTFLRL AALRTYRGRL AYLPVGRVGS KTPASPVVVQ QGPVDAHLVP   240
LEEPVPSHWT VVPDEDFVLV LALLHSHLGS EMFAAPMGRC AAGVMHLFYV RAGVSRAMLL   300
RLFLAMEKGR HMEYECPYLV YVPVVAFRLE PKDGKGVFAV DGELMVSEAV QGQVHPNYFW   360
MVSGCVEPPP SWKPQQMPPP EEPL                                         384

SEQ ID NO: 2           moltype = AA  length = 654
FEATURE                Location/Qualifiers
source                 1..654
                       mol_type = protein
                       organism = Homo sapiens
SEQUENCE: 2
MNGHLEAEEQ QDQRPDQELT GSWGHGPRST LVRAKAMAPP PPPLAASTPL LHGEFGSYPA    60
RGPRFALTLT SQALHIQRLR PKPEARPRGG LVPLAEVSGC CTLRSRSPSD SAAYFCIYTY   120
PRGRRGARRR ATRTFRADGA ATYEENRAEA QRWATALTCL LRGLPLPGDG EITPDLLPRP   180
PRLLLLVNPF GGRGLAWQWC KNHVLPMISE AGLSFNLIQT ERQNHARELV QGLSLSEWDG   240
IVTVSGDGLL HEVLNGLLDR PDWTEAVKMP VGILPCGSGN ALAGAVNQHG GFEPALGLDL   300
LLNCSLLLCR GGGHPLDLLS VTLASGSRCF SFLSVAWGFV SDVDIQSERF RALGSARFTL   360
GTVLGLATLH TYRGRLSYLP ATVEPASPTP AHSLPRAKSE LTLTPDPAPP MAHSPLHRSV   420
SDLPLPLPQP ALASPGSPEP LPILSLNGGG PELAGDWGGA GDAPLSPDPL LSSPPGSPKA   480
ALHSPVSEGA PVIPPSSGLP LPTPDARVGA STCGPPDHLL PPLGTPLPPD WTTLEGDFVL   540
MLAISPSHLG ADLVAAPHAR FDDGLVHLCW VRSGISRAAL LRLFLAMERG SHFSLGCPQL   600
GYAAARAFRL EPLTPRGVLT VDGEQVEYGP LQAQMHPGIG TLLTGPPGCP GREP         654
```